(12) United States Patent
Chien et al.

(10) Patent No.: US 12,202,902 B2
(45) Date of Patent: *Jan. 21, 2025

(54) FLT3-SPECIFIC CHIMERIC ANTIGEN RECEPTORS AND METHODS USING SAME

(71) Applicant: The United States of America, as represented by the Secretary, Department of Health and Human Services, Bethesda, MD (US)

(72) Inventors: Christopher D. Chien, Falls Church, VA (US); Terry J. Fry, Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 241 days.

This patent is subject to a terminal disclaimer.

(21) Appl. No.: 17/689,698

(22) Filed: Mar. 8, 2022

(65) Prior Publication Data
US 2022/0259317 A1 Aug. 18, 2022

Related U.S. Application Data

(63) Continuation of application No. 16/304,552, filed as application No. PCT/US2017/034691 on May 26, 2017, now Pat. No. 11,299,546.

(60) Provisional application No. 62/342,394, filed on May 27, 2016.

(51) Int. Cl.
| | |
|---|---|
| *C07K 16/28* | (2006.01) |
| *A61K 38/00* | (2006.01) |
| *A61K 39/00* | (2006.01) |
| *A61K 39/395* | (2006.01) |
| *A61P 35/00* | (2006.01) |
| *G01N 33/574* | (2006.01) |

(52) U.S. Cl.
CPC ......... *C07K 16/2863* (2013.01); *A61K 38/00* (2013.01); *A61K 39/395* (2013.01); *A61K 39/4611* (2023.05); *A61K 39/4631* (2023.05); *A61K 39/464411* (2023.05); *A61P 35/00* (2018.01); *C07K 16/2809* (2013.01); *C07K 16/2815* (2013.01); *G01N 33/57426* (2013.01); *G01N 33/57492* (2013.01); *A61K 2039/505* (2013.01); *A61K 2239/31* (2023.05); *A61K 2239/38* (2023.05); *A61K 2239/48* (2023.05); *A61K 2300/00* (2013.01); *C07K 2317/24* (2013.01); *C07K 2317/53* (2013.01); *C07K 2317/622* (2013.01); *C07K 2317/64* (2013.01); *C07K 2319/03* (2013.01); *G01N 2333/715* (2013.01)

(58) Field of Classification Search
None
See application file for complete search history.

(56) References Cited

U.S. PATENT DOCUMENTS

| | | | |
|---|---|---|---|
| 8,071,099 B2 | 12/2011 | Li et al. | |
| 11,299,546 B2* | 4/2022 | Chien | A61K 38/00 |
| 2013/0266551 A1 | 10/2013 | Campana et al. | |
| 2013/0287748 A1* | 10/2013 | June | A61P 43/00 435/328 |
| 2016/0015750 A1 | 1/2016 | Gottschalk et al. | |
| 2016/0096892 A1* | 4/2016 | Brogdon | C07K 16/30 |
| 2018/0118838 A1* | 5/2018 | Yu | A61K 39/4611 |
| 2019/0107537 A1 | 4/2019 | Chaudhary | |
| 2019/0112380 A1 | 4/2019 | Chaudhary | |
| 2023/0174614 A1* | 6/2023 | Fry | A61P 35/02 424/93.21 |

FOREIGN PATENT DOCUMENTS

| | | |
|---|---|---|
| WO | WO 2013/154760 A1 | 10/2013 |
| WO | WO 2015/084513 A1 | 6/2015 |
| WO | WO 2015/142675 A2 | 9/2015 |
| WO | WO 2017/053889 A2 | 3/2017 |

OTHER PUBLICATIONS

U.S. Appl. No. 16/304,552, filed Nov. 26, 2018.
Almagro et al., "Humanization of antibodies," *Front. Bioscience*, 13, 1619-1633 (Jan. 1, 2008).
Annesley et al., "The Biology and targeting of FLT3 in pediatric leukemia," *Front. Oncol.*, 4, 263, 1-18 pp. (2014).
Armstrong et al., "MLL translocations specify a distinct gene expression profile that distinguishes a unique leukemia," *Nat Genet.*, 30 (1), 41-47 (2002).
Asano et al., "Domain order of a bispecific diabody dramatically enhances its antitumor activity beyond structural format conversion: the case of the hEx3 diabody," *Protein Eng, Des & Sel*, 26(5): 359-367 (2013).
Birg et al., "Expression of the FMS/KIT-like gene FLT3 in human acute leukemias of the myeloid and lymphoid lineages," *Blood*, 80 (10), 2584-2593 (1992).
Birg et al., "The expression of FMS, KIT and FLT3 in hematopoietic malignancies," *Leuk Lymphoma*, 13 (3-4), 223-227 (1994).

(Continued)

*Primary Examiner* — Peter J Reddig
(74) *Attorney, Agent, or Firm* — Leydig, Voit & Mayer, Ltd.

(57) ABSTRACT

An embodiment of the invention provides a chimeric antigen receptor (CAR) comprising an antigen binding domain specific for FLT3, a transmembrane domain, and an intracellular T cell signaling domain. Nucleic acids, recombinant expression vectors, host cells, populations of cells, antibodies, or antigen binding portions thereof, and pharmaceutical compositions relating to the CARs are disclosed. Methods of detecting the presence of a proliferative disorder, e.g., cancer, in a mammal and methods of treating or preventing a proliferative disorder, e.g., cancer, in a mammal are also disclosed.

19 Claims, 11 Drawing Sheets

Specification includes a Sequence Listing.

(56) References Cited

OTHER PUBLICATIONS

Bonini et al., "Adoptive T-cell therapy for cancer: The era of engineered T cells," *Eur. J. Immunol.*, 45, 2457-2469 (2015).
Carow et al., "Expression of the hematopoietic growth factor receptor FLT3 (STK-1/Flk2) in human leukemias," *Blood*, 87, 1089-1096 (1996).
Chien et al., "Preclinical development of FLT3-redirected chimeric antigen receptor T cell Immunotherapy for acute myeloid Leukemia," *Blood*, 128 (22), Abstract No. 1072 (2016).
Clay et al., "Efficient transfer of a tumor antigen-reactive TCR to human peripheral blood lymphocytes confers anti-tumor reactivity," *J Immunol.*, 163 (1), 507-513 (1999).
Horsley et al., "Array CGH of fusion gene-positive leukemia-derived cell lines reveals cryptic regions of genomic gain and loss," *Genes Chromosomes Cancer*, 45 (6), 554-564 (2006).
International Preliminary Report on Patentability, Application No. PCT/US2017/034691, dated Dec. 6, 2018 (8 pages).
International Search Report, Application No. PCT/US2017/034691, dated Aug. 7, 2017 (6 pages).
Ferrando et al., "Gene expression signatures in MLL-rearranged T-lineage and B-precusor acute leukemias dominance of HOX dysregulation," *Blood*, 102 (1), 262-268 (2003) epublished Mar. 13, 2003.
Graf et al., "A neoepitope generated by an FLT3 internal tandem duplication (FLT3-ITD) is recognized by leukemia-reactive autologous CD8+ T cells," *Blood*, 109 (7), 2985-2988 (2007).
Lee et al., "T cells expressing CD19 chimeric antigen receptors for acute lymphoblastic leukaemia in children and young adults: a phase 1 dose-escalation trial," *Lancet.*, 385(9967): 517-528 (2015) epublished Oct. 13, 2014.
Mardiros et al., "T cells expressing CD123-specific chimeric antigen receptors exhibit specific cytolytic effector functions and anti-tumor effects against human acute myeloid leukemia," *Blood*, 122 (18), 3138-3148 (2013).
Maude et al., "Chimeric antigen receptor T cells for sustained remissions in Leukemia," *N. Eng. J. Med.*, 371 (16), 1507-1517 (2014) Author Manuscript.
Shalabi et al., "Beyond CD19: opportunities for future development of targeted immunotherapy in pediatric relapsed-refractory acute leukemia," *Frontiers in Pediatrics*, 3 (80), 1-12 (2015).
Stacchini et al., "Expression of type III receptor tyrosine kinases FLT3 and KIT and responses to their ligands by acute myeloid leukemia blasts," *Leukemia*, 10 (10), 1584-1591 (1996).
Stirewalt et al., "The role of FLT3 in haematopoietic malignancies," *Nat Rev Cancer*, 3 (9), 650-665 (2003).
Written Opinion of the International Searching Authority, Application No. PCT/US2017/034691, dated Aug. 7, 2017, 6 pages.
Zhao et al., "Primary human lymphocytes transduced with ny-eso-1 antigen-specific TCR genes recognize and kill diverse human tumor cell lines," *J. Immunol.*, 174 (7), 4415-4423 (2005) Author Manuscript.
Burns et al., "A high molecular weight melanoma-associated antigen-specific chimeric antigen receptor redirects lymphocytes to target human melanomas," *Cancer Res.*, 70(8): 3027-3033 (Apr. 2010).
Caraballo Galva et al., "Engineering T cells for immunotherapy of primary human hepatocellular carcinoma," *J Genet Genomics*, 47(1): 1-15 (Jan. 2020), available online Jan. 28, 2020.
Desplancq et al., "Multimerization behaviour of single chain Fv variants for the tumour-binding antibody B72.3," *Protein Eng*, 7(8): 1027-1033 (Aug. 1994).
Fernandez-Quintero et al., "$V_H$-$V_L$ interdomain dynamics observed by computer simulations and NMR." *Proteins*, 88(7): 830-839 (Jul. 2020).
Fujiwara et al., "Impact of scFv structure in chimeric antigen receptor on receptor expression efficiency and antigen recognition properties," *Biochem Biophys Res Commun.*, 527(2): 350-357 (Jun. 2020), available online Mar. 23, 2020.
Geng et al., "Binding activity difference of anti-CD20 scFv-Fc fusion protein derived from variable domain exchange," *Cel Mol Immunol.*, 3(6): 439-443 (Dec. 2006).
Jena et al., "Redirecting T-cell specificity by introducing a tumor-specific chimeric antigen receptor," *Blood*, 116(7): 1035-1044 (Aug. 2010).
Johnson et al., "Rational development and characterization of humanized ant-EGFR variant III chimeric antigen receptor T cells for glioblastoma," *Sci Transl Med.*, 7(275): 275ra22, 30 pp. (Feb. 2015) Author manuscript published on PubMed.
Long et al., "4-1BB costimulation ameliorates T cell exhaustion induced by tonic signaling of chimeric antigen receptors," *Nat Med*, 21(6) 581-590 (Jun. 2015), available online May 4, 2015.
Lu et al., "The effect of variable domain orientation and arrangement on the antigen-binding activity of a recombinant human bispecific diabody," *Biochem Biophys Res Commun.*, 318(2): 507-513 (May 2004), available online Apr. 22, 2004.
Myers et al., "Humanized CD19-targeted chimeric antigen receptor (CAR) T cells in CAR-naïve and CAR-exposed children and young adults with relapsed or refractory acute lymphoblastic leukemia," *J Clin Oncol*, JCO2003458, 13 pp. (Jun. 2021).
Wagner et al., "Immunogenicity of Car T cells in cancer therapy," *Nat Rev Clin Oncol*, 18: 379-393 (Jun. 2021).

\* cited by examiner

SEQUENCE LISTING

```
<160> NUMBER OF SEQ ID NOS: 30

<210> SEQ ID NO 1
<211> LENGTH: 490
<212> TYPE: PRT
<213> ORGANISM: Artificial Sequence
<220> FEATURE:
<223> OTHER INFORMATION: SYNTHETIC

<400> SEQUENCE: 1

Met Leu Leu Val Thr Ser Leu Leu Leu Cys Glu Leu Pro His Pro Ala
1               5                   10                  15

Phe Leu Leu Ile Pro Glu Val Gln Leu Val Gln Ser Gly Ala Glu Val
            20                  25                  30

Lys Lys Pro Gly Ser Ser Val Lys Val Ser Cys Lys Ala Ser Gly Gly
        35                  40                  45

Thr Phe Ser Ser Tyr Ala Ile Ser Trp Val Arg Gln Ala Pro Gly Gln
    50                  55                  60

Gly Leu Glu Trp Met Gly Gly Ile Ile Pro Ile Phe Gly Thr Ala Asn
65                  70                  75                  80

Tyr Ala Gln Lys Phe Gln Gly Arg Val Thr Ile Thr Ala Asp Lys Ser
                85                  90                  95

Thr Ser Thr Ala Tyr Met Glu Leu Ser Ser Leu Arg Ser Glu Asp Thr
            100                 105                 110

Ala Val Tyr Tyr Cys Ala Thr Phe Ala Leu Phe Gly Phe Arg Glu Gln
        115                 120                 125

Ala Phe Asp Ile Trp Gly Gln Gly Thr Thr Val Thr Val Ser Ser Gly
```

```
                130                 135                 140
Gly Gly Gly Ser Gly Gly Gly Ser Gly Gly Gly Ser Asp Ile
145                 150                 155                 160

Gln Met Thr Gln Ser Pro Ser Leu Ser Ala Ser Val Gly Asp Arg
                165                 170                 175

Val Thr Ile Thr Cys Arg Ala Ser Gln Ser Ile Ser Ser Tyr Leu Asn
            180                 185                 190

Trp Tyr Gln Gln Lys Pro Gly Lys Ala Pro Lys Leu Leu Ile Tyr Ala
        195                 200                 205

Ala Ser Ser Leu Gln Ser Gly Val Pro Ser Arg Phe Ser Gly Ser Gly
    210                 215                 220

Ser Gly Thr Asp Phe Thr Leu Thr Ile Ser Ser Leu Gln Pro Glu Asp
225                 230                 235                 240

Leu Ala Thr Tyr Tyr Cys Gln Gln Ser Tyr Ser Thr Pro Phe Thr Phe
                245                 250                 255

Gly Pro Gly Thr Lys Val Asp Ile Lys Ser Gly Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 2
<211> LENGTH: 731
<212> TYPE: PRT
<213> ORGANISM: Artificial Sequence
<220> FEATURE:
<223> OTHER INFORMATION: SYNTHETIC

<400> SEQUENCE: 2

Met Leu Leu Val Thr Ser Leu Leu Leu Cys Glu Leu Pro His Pro Ala
```

-continued

```
1               5                   10                  15
Phe Leu Leu Ile Pro Glu Val Gln Leu Val Gln Ser Gly Ala Glu Val
                20                  25                  30
Lys Lys Pro Gly Ser Ser Val Lys Val Ser Cys Lys Ala Ser Gly Gly
                35                  40                  45
Thr Phe Ser Ser Tyr Ala Ile Ser Trp Val Arg Gln Ala Pro Gly Gln
                50                  55                  60
Gly Leu Glu Trp Met Gly Gly Ile Ile Pro Ile Phe Gly Thr Ala Asn
65                  70                  75                  80
Tyr Ala Gln Lys Phe Gln Gly Arg Val Thr Ile Thr Ala Asp Lys Ser
                85                  90                  95
Thr Ser Thr Ala Tyr Met Glu Leu Ser Ser Leu Arg Ser Glu Asp Thr
                100                 105                 110
Ala Val Tyr Tyr Cys Ala Thr Phe Ala Leu Phe Gly Phe Arg Glu Gln
                115                 120                 125
Ala Phe Asp Ile Trp Gly Gln Gly Thr Thr Val Thr Val Ser Ser Gly
                130                 135                 140
Gly Gly Gly Ser Gly Gly Gly Ser Gly Gly Gly Ser Asp Ile
145                 150                 155                 160
Gln Met Thr Gln Ser Pro Ser Ser Leu Ser Ala Ser Val Gly Asp Arg
                165                 170                 175
Val Thr Ile Thr Cys Arg Ala Ser Gln Ser Ile Ser Ser Tyr Leu Asn
                180                 185                 190
Trp Tyr Gln Gln Lys Pro Gly Lys Ala Pro Lys Leu Leu Ile Tyr Ala
                195                 200                 205
Ala Ser Ser Leu Gln Ser Gly Val Pro Ser Arg Phe Ser Gly Ser Gly
                210                 215                 220
Ser Gly Thr Asp Phe Thr Leu Thr Ile Ser Ser Leu Gln Pro Glu Asp
225                 230                 235                 240
Leu Ala Thr Tyr Tyr Cys Gln Gln Ser Tyr Ser Thr Pro Phe Thr Phe
                245                 250                 255
Gly Pro Gly Thr Lys Val Asp Ile Lys Ser Gly Leu Glu Asp Pro Ala
                260                 265                 270
Glu Pro Lys Ser Pro Asp Lys Thr His Thr Cys Pro Pro Cys Pro Ala
                275                 280                 285
Pro Glu Leu Leu Gly Gly Pro Ser Val Phe Leu Phe Pro Pro Lys Pro
                290                 295                 300
Lys Asp Thr Leu Met Ile Ser Arg Thr Pro Glu Val Thr Cys Val Val
305                 310                 315                 320
Val Asp Val Ser His Glu Asp Pro Glu Val Lys Phe Asn Trp Tyr Val
                325                 330                 335
Asp Gly Val Glu Val His Asn Ala Lys Thr Lys Pro Arg Glu Glu Gln
                340                 345                 350
Tyr Asn Ser Thr Tyr Arg Val Val Ser Val Leu Thr Val Leu His Gln
                355                 360                 365
Asp Trp Leu Asn Gly Lys Glu Tyr Lys Cys Lys Val Ser Asn Lys Ala
                370                 375                 380
Leu Pro Ala Pro Ile Glu Lys Thr Ile Ser Lys Ala Lys Gly Gln Pro
385                 390                 395                 400
Arg Glu Pro Gln Val Tyr Thr Leu Pro Pro Ser Arg Asp Glu Leu Thr
                405                 410                 415
Lys Asn Gln Val Ser Leu Thr Cys Leu Val Lys Gly Phe Tyr Pro Ser
                420                 425                 430
```

Asp Ile Ala Val Glu Trp Glu Ser Asn Gly Gln Pro Glu Asn Asn Tyr
            435                 440                 445

Lys Thr Thr Pro Pro Val Leu Asp Ser Asp Gly Ser Phe Phe Leu Tyr
450                 455                 460

Ser Lys Leu Thr Val Asp Lys Ser Arg Trp Gln Gln Gly Asn Val Phe
465                 470                 475                 480

Ser Cys Ser Val Met His Glu Ala Leu His Asn His Tyr Thr Gln Lys
                485                 490                 495

Ser Leu Ser Leu Ser Pro Gly Lys Lys Asp Pro Lys Thr Thr Thr Pro
            500                 505                 510

Ala Pro Arg Pro Pro Thr Pro Ala Pro Thr Ile Ala Ser Gln Pro Leu
            515                 520                 525

Ser Leu Arg Pro Glu Ala Cys Arg Pro Ala Ala Gly Gly Ala Val His
            530                 535                 540

Thr Arg Gly Leu Asp Phe Ala Cys Asp Ile Tyr Ile Trp Ala Pro Leu
545                 550                 555                 560

Ala Gly Thr Cys Gly Val Leu Leu Leu Ser Leu Val Ile Thr Leu Tyr
                565                 570                 575

Cys Lys Arg Gly Arg Lys Lys Leu Leu Tyr Ile Phe Lys Gln Pro Phe
            580                 585                 590

Met Arg Pro Val Gln Thr Thr Gln Glu Glu Asp Gly Cys Ser Cys Arg
            595                 600                 605

Phe Pro Glu Glu Glu Glu Gly Gly Cys Glu Leu Arg Val Lys Phe Ser
610                 615                 620

Arg Ser Ala Asp Ala Pro Ala Tyr Lys Gln Gly Gln Asn Gln Leu Tyr
625                 630                 635                 640

Asn Glu Leu Asn Leu Gly Arg Arg Glu Glu Tyr Asp Val Leu Asp Lys
                645                 650                 655

Arg Arg Gly Arg Asp Pro Glu Met Gly Gly Lys Pro Arg Arg Lys Asn
            660                 665                 670

Pro Gln Glu Gly Leu Tyr Asn Glu Leu Gln Lys Asp Lys Met Ala Glu
            675                 680                 685

Ala Tyr Ser Glu Ile Gly Met Lys Gly Glu Arg Arg Arg Gly Lys Gly
            690                 695                 700

His Asp Gly Leu Tyr Gln Gly Leu Ser Thr Ala Thr Lys Asp Thr Tyr
705                 710                 715                 720

Asp Ala Leu His Met Gln Ala Leu Pro Pro Arg
                725                 730

<210> SEQ ID NO 3
<211> LENGTH: 1
<212> TYPE: PRT
<213> ORGANISM: Artificial Sequence
<220> FEATURE:
<223> OTHER INFORMATION: SYNTHETIC

<400> SEQUENCE: 3

Met
1

<210> SEQ ID NO 4
<211> LENGTH: 20
<212> TYPE: PRT
<213> ORGANISM: Artificial Sequence
<220> FEATURE:
<223> OTHER INFORMATION: SYNTHETIC -continued

```
<400> SEQUENCE: 4

Leu Val Thr Ser Leu Leu Leu Cys Glu Leu Pro His Pro Ala Phe
1               5                   10                  15

Leu Leu Ile Pro
            20

<210> SEQ ID NO 5
<211> LENGTH: 25
<212> TYPE: PRT
<213> ORGANISM: Artificial Sequence
<220> FEATURE:
<223> OTHER INFORMATION: SYNTHETIC

<400> SEQUENCE: 5

Glu Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 6
<211> LENGTH: 10
<212> TYPE: PRT
<213> ORGANISM: Artificial Sequence
<220> FEATURE:
<223> OTHER INFORMATION: SYNTHETIC

<400> SEQUENCE: 6

Gly Gly Thr Phe Ser Ser Tyr Ala Ile Ser
1               5                   10

<210> SEQ ID NO 7
<211> LENGTH: 14
<212> TYPE: PRT
<213> ORGANISM: Artificial Sequence
<220> FEATURE:
<223> OTHER INFORMATION: SYNTHETIC

<400> SEQUENCE: 7

Trp Val Arg Gln Ala Pro Gly Gln Gly Leu Glu Trp Met Gly
1               5                   10

<210> SEQ ID NO 8
<211> LENGTH: 17
<212> TYPE: PRT
<213> ORGANISM: Artificial Sequence
<220> FEATURE:
<223> OTHER INFORMATION: SYNTHETIC

<400> SEQUENCE: 8

Gly Ile Ile Pro Ile Phe Gly Thr Ala Asn Tyr Ala Gln Lys Phe Gln
1               5                   10                  15

Gly

<210> SEQ ID NO 9
<211> LENGTH: 32
<212> TYPE: PRT
<213> ORGANISM: Artificial Sequence
<220> FEATURE:
<223> OTHER INFORMATION: SYNTHETIC

<400> SEQUENCE: 9

Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Ala Thr
```

-continued

```
                   20                  25                  30
```

<210> SEQ ID NO 10
<211> LENGTH: 13
<212> TYPE: PRT
<213> ORGANISM: Artificial Sequence
<220> FEATURE:
<223> OTHER INFORMATION: SYNTHETIC

<400> SEQUENCE: 10

```
Phe Ala Leu Phe Gly Phe Arg Glu Gln Ala Phe Asp Ile
1               5                   10
```

<210> SEQ ID NO 11
<211> LENGTH: 11
<212> TYPE: PRT
<213> ORGANISM: Artificial Sequence
<220> FEATURE:
<223> OTHER INFORMATION: SYNTHETIC

<400> SEQUENCE: 11

```
Trp Gly Gln Gly Thr Thr Val Thr Val Ser Ser
1               5                   10
```

<210> SEQ ID NO 12
<211> LENGTH: 15
<212> TYPE: PRT
<213> ORGANISM: Artificial Sequence
<220> FEATURE:
<223> OTHER INFORMATION: SYNTHETIC

<400> SEQUENCE: 12

```
Gly Gly Gly Gly Ser Gly Gly Gly Gly Ser Gly Gly Gly Gly Ser
1               5                   10                  15
```

<210> SEQ ID NO 13
<211> LENGTH: 23
<212> TYPE: PRT
<213> ORGANISM: Artificial Sequence
<220> FEATURE:
<223> OTHER INFORMATION: SYNTHETIC

<400> SEQUENCE: 13

```
Asp Ile Gln Met Thr Gln Ser Pro Ser Ser Leu Ser Ala Ser Val Gly
1               5                   10                  15

Asp Arg Val Thr Ile Thr Cys
            20
```

<210> SEQ ID NO 14
<211> LENGTH: 11
<212> TYPE: PRT
<213> ORGANISM: Artificial Sequence
<220> FEATURE:
<223> OTHER INFORMATION: SYNTHETIC

<400> SEQUENCE: 14

```
Arg Ala Ser Gln Ser Ile Ser Ser Tyr Leu Asn
1               5                   10
```

<210> SEQ ID NO 15
<211> LENGTH: 15
<212> TYPE: PRT
<213> ORGANISM: Artificial Sequence
<220> FEATURE:
<223> OTHER INFORMATION: SYNTHETIC

<400> SEQUENCE: 15

Trp Tyr Gln Gln Lys Pro Gly Lys Ala Pro Lys Leu Leu Ile Tyr
1               5                   10                  15

<210> SEQ ID NO 16
<211> LENGTH: 7
<212> TYPE: PRT
<213> ORGANISM: Artificial Sequence
<220> FEATURE:
<223> OTHER INFORMATION: SYNTHETIC

<400> SEQUENCE: 16

Ala Ala Ser Ser Leu Gln Ser
1               5

<210> SEQ ID NO 17
<211> LENGTH: 32
<212> TYPE: PRT
<213> ORGANISM: Artificial Sequence
<220> FEATURE:
<223> OTHER INFORMATION: SYNTHETIC

<400> SEQUENCE: 17

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Leu Ala Thr Tyr Tyr Cys
                20                  25                  30

<210> SEQ ID NO 18
<211> LENGTH: 9
<212> TYPE: PRT
<213> ORGANISM: Artificial Sequence
<220> FEATURE:
<223> OTHER INFORMATION: SYNTHETIC

<400> SEQUENCE: 18

Gln Gln Ser Tyr Ser Thr Pro Phe Thr
1               5

<210> SEQ ID NO 19
<211> LENGTH: 10
<212> TYPE: PRT
<213> ORGANISM: Artificial Sequence
<220> FEATURE:
<223> OTHER INFORMATION: SYNTHETIC

<400> SEQUENCE: 19

Phe Gly Pro Gly Thr Lys Val Asp Ile Lys
1               5                   10

<210> SEQ ID NO 20
<211> LENGTH: 2
<212> TYPE: PRT
<213> ORGANISM: Artificial Sequence
<220> FEATURE:
<223> OTHER INFORMATION: SYNTHETIC

<400> SEQUENCE: 20

Ser Gly
1

<210> SEQ ID NO 21
<211> LENGTH: 4
<212> TYPE: PRT
<213> ORGANISM: Artificial Sequence
<220> FEATURE:
<223> OTHER INFORMATION: SYNTHETIC

<400> SEQUENCE: 21

Leu Glu Asp Pro
1

<210> SEQ ID NO 22
<211> LENGTH: 126
<212> TYPE: PRT
<213> ORGANISM: Artificial Sequence
<220> FEATURE:
<223> OTHER INFORMATION: SYNTHETIC

<400> SEQUENCE: 22

Ala Glu Pro Lys Ser Pro Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys
        115                 120                 125

<210> SEQ ID NO 23
<211> LENGTH: 107
<212> TYPE: PRT
<213> ORGANISM: Artificial Sequence
<220> FEATURE:
<223> OTHER INFORMATION: SYNTHETIC

<400> SEQUENCE: 23

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 24
<211> LENGTH: 4
<212> TYPE: PRT
<213> ORGANISM: Artificial Sequence
<220> FEATURE:
<223> OTHER INFORMATION: SYNTHETIC

```
<400> SEQUENCE: 24

Lys Asp Pro Lys
1

<210> SEQ ID NO 25
<211> LENGTH: 45
<212> TYPE: PRT
<213> ORGANISM: Artificial Sequence
<220> FEATURE:
<223> OTHER INFORMATION: SYNTHETIC

<400> SEQUENCE: 25

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp
            35                  40                  45

<210> SEQ ID NO 26
<211> LENGTH: 24
<212> TYPE: PRT
<213> ORGANISM: Artificial Sequence
<220> FEATURE:
<223> OTHER INFORMATION: SYNTHETIC

<400> SEQUENCE: 26

Ile Tyr Ile Trp Ala Pro Leu Ala Gly Thr Cys Gly Val Leu Leu Leu
1               5                   10                  15

Ser Leu Val Ile Thr Leu Tyr Cys
                20

<210> SEQ ID NO 27
<211> LENGTH: 42
<212> TYPE: PRT
<213> ORGANISM: Artificial Sequence
<220> FEATURE:
<223> OTHER INFORMATION: SYNTHETIC

<400> SEQUENCE: 27

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
            35                  40

<210> SEQ ID NO 28
<211> LENGTH: 112
<212> TYPE: PRT
<213> ORGANISM: Artificial Sequence
<220> FEATURE:
<223> OTHER INFORMATION: SYNTHETIC

<400> SEQUENCE: 28

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
```

```
                    50                  55                  60
Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
            100                 105                 110
```

<210> SEQ ID NO 29
<211> LENGTH: 469
<212> TYPE: PRT
<213> ORGANISM: Artificial Sequence
<220> FEATURE:
<223> OTHER INFORMATION: SYNTHETIC

<400> SEQUENCE: 29

```
Glu Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Lys Phe
     50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Thr Phe Ala Leu Phe Gly Phe Arg Glu Gln Ala Phe Asp Ile Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Gly Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

Arg Ala Ser Gln Ser Ile Ser Ser Tyr Leu Asn Trp Tyr Gln Gln Lys
                165                 170                 175

Pro Gly Lys Ala Pro Lys Leu Leu Ile Tyr Ala Ala Ser Ser Leu Gln
            180                 185                 190

Ser Gly Val Pro Ser Arg Phe Ser Gly Ser Gly Ser Gly Thr Asp Phe
        195                 200                 205

Thr Leu Thr Ile Ser Ser Leu Gln Pro Glu Asp Leu Ala Thr Tyr Tyr
    210                 215                 220

Cys Gln Gln Ser Tyr Ser Thr Pro Phe Thr Phe Gly Pro Gly Thr Lys
225                 230                 235                 240

Val Asp Ile Lys Ser Gly Thr Thr Thr Pro Ala Pro Arg Pro Pro Thr
                245                 250                 255

Pro Ala Pro Thr Ile Ala Ser Gln Pro Leu Ser Leu Arg Pro Glu Ala
            260                 265                 270

Cys Arg Pro Ala Ala Gly Gly Ala Val His Thr Arg Gly Leu Asp Phe
        275                 280                 285

Ala Cys Asp Ile Tyr Ile Trp Ala Pro Leu Ala Gly Thr Cys Gly Val
    290                 295                 300

Leu Leu Leu Ser Leu Val Ile Thr Leu Tyr Cys Lys Arg Gly Arg Lys
```

```
            305                 310                 315                 320
Lys Leu Leu Tyr Ile Phe Lys Gln Pro Phe Met Arg Pro Val Gln Thr
                    325                 330                 335

Thr Gln Glu Glu Asp Gly Cys Ser Cys Arg Phe Pro Glu Glu Glu Glu
                340                 345                 350

Gly Gly Cys Glu Leu Arg Val Lys Phe Ser Arg Ser Ala Asp Ala Pro
            355                 360                 365

Ala Tyr Lys Gln Gly Gln Asn Gln Leu Tyr Asn Glu Leu Asn Leu Gly
        370                 375                 380

Arg Arg Glu Glu Tyr Asp Val Leu Asp Lys Arg Gly Arg Asp Pro
385                 390                 395                 400

Glu Met Gly Gly Lys Pro Arg Arg Lys Asn Pro Gln Glu Gly Leu Tyr
                405                 410                 415

Asn Glu Leu Gln Lys Asp Lys Met Ala Glu Ala Tyr Ser Glu Ile Gly
                420                 425                 430

Met Lys Gly Glu Arg Arg Arg Gly Lys Gly His Asp Gly Leu Tyr Gln
            435                 440                 445

Gly Leu Ser Thr Ala Thr Lys Asp Thr Tyr Asp Ala Leu His Met Gln
        450                 455                 460

Ala Leu Pro Pro Arg
465

<210> SEQ ID NO 30
<211> LENGTH: 710
<212> TYPE: PRT
<213> ORGANISM: Artificial Sequence
<220> FEATURE:
<223> OTHER INFORMATION: SYNTHETIC

<400> SEQUENCE: 30

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Phe Ala Leu Phe Gly Phe Arg Glu Gln Ala Phe Asp Ile Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

Arg Ala Ser Gln Ser Ile Ser Ser Tyr Leu Asn Trp Tyr Gln Gln Lys
                165                 170                 175

Pro Gly Lys Ala Pro Lys Leu Leu Ile Tyr Ala Ala Ser Ser Leu Gln
            180                 185                 190

Ser Gly Val Pro Ser Arg Phe Ser Gly Ser Gly Ser Gly Thr Asp Phe
```

```
            195                 200                 205
Thr Leu Thr Ile Ser Ser Leu Gln Pro Glu Asp Leu Ala Thr Tyr Tyr
    210                 215                 220

Cys Gln Gln Ser Tyr Ser Thr Pro Phe Thr Phe Gly Pro Gly Thr Lys
225                 230                 235                 240

Val Asp Ile Lys Ser Gly Leu Glu Asp Pro Ala Glu Pro Lys Ser Pro
                245                 250                 255

Asp Lys Thr His Thr Cys Pro Pro Cys Pro Ala Pro Glu Leu Leu Gly
            260                 265                 270

Gly Pro Ser Val Phe Leu Phe Pro Pro Lys Pro Lys Asp Thr Leu Met
        275                 280                 285

Ile Ser Arg Thr Pro Glu Val Thr Cys Val Val Val Asp Val Ser His
    290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
        355                 360                 365

Glu Lys Thr Ile Ser Lys Ala Lys Gly Gln Pro Arg Glu Pro Gln Val
    370                 375                 380

Tyr Thr Leu Pro Pro Ser Arg Asp Glu Leu Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
            420                 425                 430

Val Leu Asp Ser Asp Gly Ser Phe Phe Leu Tyr Ser Lys Leu Thr Val
        435                 440                 445

Asp Lys Ser Arg Trp Gln Gln Gly Asn Val Phe Ser Cys Ser Val Met
    450                 455                 460

His Glu Ala Leu His Asn His Tyr Thr Gln Lys Ser Leu Ser Leu Ser
465                 470                 475                 480

Pro Gly Lys Lys Asp Pro Lys Thr Thr Thr Pro Ala Pro Arg Pro Pro
                485                 490                 495

Thr Pro Ala Pro Thr Ile Ala Ser Gln Pro Leu Ser Leu Arg Pro Glu
            500                 505                 510

Ala Cys Arg Pro Ala Ala Gly Gly Ala Val His Thr Arg Gly Leu Asp
        515                 520                 525

Phe Ala Cys Asp Ile Tyr Ile Trp Ala Pro Leu Ala Gly Thr Cys Gly
    530                 535                 540

Val Leu Leu Leu Ser Leu Val Ile Thr Leu Tyr Cys Lys Arg Gly Arg
545                 550                 555                 560

Lys Lys Leu Leu Tyr Ile Phe Lys Gln Pro Phe Met Arg Pro Val Gln
                565                 570                 575

Thr Thr Gln Glu Glu Asp Gly Cys Ser Cys Arg Phe Pro Glu Glu Glu
            580                 585                 590

Glu Gly Gly Cys Glu Leu Arg Val Lys Phe Ser Arg Ser Ala Asp Ala
        595                 600                 605

Pro Ala Tyr Lys Gln Gly Gln Asn Gln Leu Tyr Asn Glu Leu Asn Leu
    610                 615                 620
```

```
Gly Arg Arg Glu Glu Tyr Asp Val Leu Asp Lys Arg Arg Gly Arg Asp
625                 630                 635                 640

Pro Glu Met Gly Gly Lys Pro Arg Arg Lys Asn Pro Gln Glu Gly Leu
                645                 650                 655

Tyr Asn Glu Leu Gln Lys Asp Lys Met Ala Glu Ala Tyr Ser Glu Ile
            660                 665                 670

Gly Met Lys Gly Glu Arg Arg Arg Gly Lys Gly His Asp Gly Leu Tyr
        675                 680                 685

Gln Gly Leu Ser Thr Ala Thr Lys Asp Thr Tyr Asp Ala Leu His Met
    690                 695                 700

Gln Ala Leu Pro Pro Arg
705             710
```

FLT3-SPECIFIC CHIMERIC ANTIGEN RECEPTORS AND METHODS USING SAME

CROSS-REFERENCE TO RELATED APPLICATIONS

This patent application is a continuation application of co-pending U.S. patent application Ser. No. 16/304,552, filed Nov. 26, 2018, which is the U.S. national phase of International Patent Application No. PCT/US2017/034691, filed May 26, 2017, which claims the benefit of U.S. Provisional Patent Application No. 62/342,394, filed May 27, 2016, each of which is incorporated by reference in its entirety herein.

STATEMENT REGARDING FEDERALLY SPONSORED RESEARCH AND DEVELOPMENT

This invention was made with government support from the Intramural Research Program of the National Institutes of Health, National Cancer Institute, Center for Cancer Research under Project No. ZIA BC 011295.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 30,252 Byte ASCII (Text) file named "759637 ST25.txt" created on Mar. 8, 2022.

BACKGROUND OF THE INVENTION

There are still leukemic patient populations where standard therapies are sub-optimal. For example, patients with infant pre-B cell precursor acute lymphoblastic leukemia (ALL) or acute myeloid leukemia (AML) have survival rates of less than 40 and 60%, respectively.

Accordingly, there exists an unmet need for additional treatments for cancer.

BRIEF SUMMARY OF THE INVENTION

Embodiments of the invention provide chimeric antigen receptors (CARs) comprising an antigen binding domain specific for FLT3, a transmembrane domain, and an intracellular T cell signaling domain. The CAR may further comprise a 4-1BB intracellular domain, a spacer, or both.

Further embodiments of the invention provide related nucleic acids, recombinant expression vectors, host cells, populations of cells, antibodies, or antigen binding portions thereof, and pharmaceutical compositions relating to the CARs of the invention.

Additional embodiments of the invention provide methods of detecting the presence of a proliferative disorder, e.g., cancer, and methods of treating or preventing a proliferative disorder, e.g., cancer, in a mammal.

DETAILED DESCRIPTION OF THE INVENTION

Figure 1:
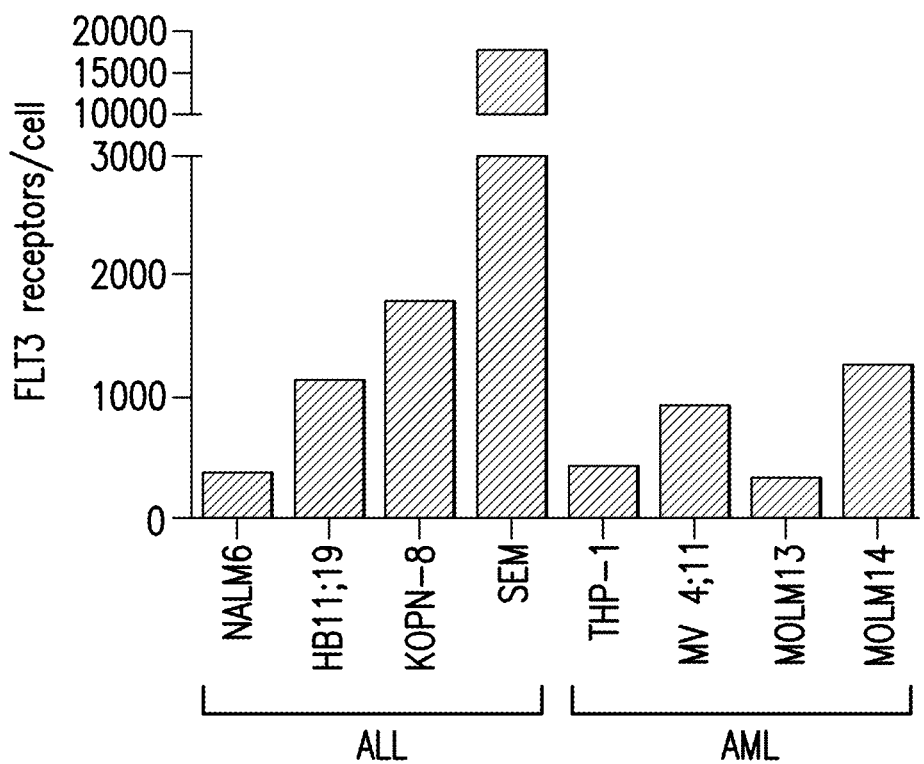
FIG. 1 is a bar graph showing FLT3 is expressed on acute lymphoblastic and acute myeloid leukemia cell lines.

ALL represents a common oncologic diagnosis in children. Substantial progress has been made in the upfront chemotherapy for pediatric ALL such that most patients will be cured. Nonetheless, ALL remains a common cause of death from cancer in children due to relapse of disease that no longer responds to cytotoxic chemotherapy, or due to refractoriness to upfront treatment. Furthermore, long-term therapy-induced morbidity remains a major issue, particularly in those patients deemed to be high-risk for relapse and thus treated with more intense regimens under current risk-adapted protocols. In adults, ALL occurs less commonly than in children, but the prognosis for adult ALL is worse than in children undergoing standard cytotoxic chemotherapy. Treatment of young adults on pediatric-type regimens has improved outcome but not to the level achieved in children.

The adoptive cell transfer (ADT or ACT) of T cells genetically modified to express chimeric antigen receptors (CARs) targeting antigens expressed on lymphoid cells have demonstrated potent activity in B cell malignancies, including ALL, resulting in remissions in chemotherapy refractory patients. The surface protein being targeted in the majority of these trials is the CD19 antigen that is expressed on both malignant and non-malignant B cells. However, not all patients respond and relapses occur, in some cases due to loss of CD19 expression. Loss of CD19 also has been observed after treatment with bispecific antibody-based reagents targeting CD19 and CD3.

Patients with infant ALL or AML express high levels of FMS-like tyrosine kinase 3 (FLT3). FLT3 is also known as Fms-Related Tyrosine Kinase 3, Stem Cell Tyrosine Kinase 1, FL Cytokine Receptor, CD135 Antigen, FLK-2, STK1, and Fetal Liver Kinase 2. FLT3 is frequently mutated in AML, causing activation of the pathway, and is thought to be a major driver of disease. Thus, down-modulation of FLT3 will be an improbable escape mechanism. Additionally, the mutations are found in the intracellular domain of the receptor so immune cells expressing FLT3 CARs will be able to target both wild type and mutant forms of FLT3 allowing for broad targeting of both infant ALL and AML and may target any FLT3-overexpressing leukemia.

An embodiment of the invention provides chimeric antigen receptors (CARs) comprising an antigen binding domain specific for FLT3, a transmembrane domain, and an intracellular T cell signaling domain. The CAR may further comprise a 4-1BB intracellular domain, a spacer, or both.

A chimeric antigen receptor (CAR) is an artificially constructed hybrid protein or polypeptide containing the antigen binding domain of an antibody (e.g., single chain variable fragment (scFv)) linked to T-cell signaling domains. Characteristics of CARs include their ability to redirect T-cell specificity and reactivity toward a selected target in a non-MHC-restricted manner, exploiting the antigen-binding properties of monoclonal antibodies. The non-MHC-restricted antigen recognition gives T cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains.

The phrases "have antigen specificity" and "elicit antigen-specific response" as used herein means that the CAR can specifically bind to and immunologically recognize an antigen, such that binding of the CAR to the antigen elicits an immune response.

Without being bound to a particular theory or mechanism, it is believed that by eliciting an antigen-specific response against FLT3, the inventive CARs provide for one or more of the following: targeting and destroying FLT3-expressing cancer cells, reducing or eliminating cancer cells, facilitating infiltration of immune cells to tumor site(s), and enhancing/extending anti-cancer responses.

An embodiment of the invention provides a CAR comprising an antigen binding domain specific for FLT3, based on antibodies, e.g., NC7. NC7 is described in U.S. Pat. No. 8,071,099, which is incorporated herein by reference in its entirety. The scFv comprises a light chain variable region and a heavy chain variable region. In embodiments of the invention, the light chain and heavy chain may comprise any suitable combination of light chain and heavy chain sequences, e.g., as listed in Table 1 below.

In an embodiment, the CAR may have a multispecific antigen binding domain. For example, the CAR may be specific for FLT3 and at least one other target, e.g., a leukemia target such as CD19 or CD22 for ALL, or CD33 or CD123 for AML.

In an embodiment, the antigen binding domain comprises a linker. The linker connects the heavy chain variable region and the light chain variable region of the antigen binding domain. Any linker suitable for linking the heavy chain variable region and the light chain variable region may be used in the antigen binding domains of the invention. In an embodiment, the linker comprises, consists of, or consists essentially of a glycine-serine linker domain. Preferably, the antigen binding domain comprises a scFv comprising a heavy chain variable region, a light chain variable region, and a linker. In embodiments of the invention, the light chain, heavy chain, and linker may comprise any suitable combination of light chain, heavy chain, and linker sequences as listed in Table 1 below.

In an embodiment of the invention, the CAR comprises, consists of, or consists essentially of the sequence:

(SEQ ID NO: 1)
MLLVTSLLLCELPHPAFLLIPEVQLVQSGAEVKKPGSSVKVSCKASGGTF

SSYAISWVRQAPGQGLEWMGGIIPIFGTANYAQKFQGRVTITADKSTSTA

YMELSSLRSEDTAVYYCATFALFGFREQAFDIWGQGTTVTVSSGGGGSGG

GGSGGGGSDIQMTQSPSSLSASVGDRVTITCRASQSISSYLNVVYQQKPG

KAPKLLIYAASSLQSGVPSRFSGSGSGTDFTLTISSLQPEDLATYYCQQS

YSTPFTFGPGTKVDIKSGTTTPAPRPPTPAPTIASQPLSLRPEACRPAAG

GAVHTRGLDFACDIYIWAPLAGTCGVLLLSLVITLYCKRGRKKLLYIFKQ

PFMRPVQTTQEEDGCSCRFPEEEEGGCELRVKFSRSADAPAYKQGQNQLY

NELNLGRREEYDVLDKRRGRDPEMGGKPRRKNPQEGLYNELQKDKMAEAY

SEIGMKGERRRGKGHDGLYQGLSTATKDTYDALHMQALPPR.

In another embodiment of the invention, the CAR comprises, consists of, or consists essentially of the sequence:

(SEQ ID NO: 2)
MLLVTSLLLCELPHPAFLLIPEVQLVQSGAEVKKPGSSVKVSCKASGGTF

SSYAISWVRQAPGQGLEWMGGIIPIFGTANYAQKFQGRVTITADKSTSTA

YMELSSLRSEDTAVYYCATFALFGFREQAFDIWGQGTTVTVSSGGGGSGG

GGSGGGGSDIQMTQSPSSLSASVGDRVTITCRASQSISSYLNVVYQQKPG

KAPKLLIYAASSLQSGVPSRFSGSGSGTDFTLTISSLQPEDLATYYCQQS

YSTPFTFGPGTKVDIKSGLEDPAEPKSPDKTHTCPPCPAPELLGGPSVFL

FPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENNYK

TTPPVLDSDGSFFLYSKLTVDKSRWQQGNVFSCSVMHEALHNHYTQKSLS

LSPGKKDPKTTTPAPRPPTPAPTIASQPLSLRPEACRPAAGGAVHTRGLD

FACDIYIWAPLAGTCGVLLLSLVITLYCKRGRKKLLYIFKQPFMRPVQTT

QEEDGCSCRFPEEEEGGCELRVKFSRSADAPAYKQGQNQLYNELNLGRRE

EYDVLDKRRGRDPEMGGKPRRKNPQEGLYNELQKDKMAEAYSEIGMKGER

RRGKGHDGLYQGLSTATKDTYDALHMQALPPR.

In an embodiment, the antigen binding domain comprises a leader/signal sequence. The leader sequence may be positioned at the amino terminus of the heavy chain variable region. The leader sequence may comprise any suitable leader sequence. In embodiments of the invention, the leader/signal sequence may comprise the sequence as listed in Table 1 below. In the mature form of the T cell, the leader sequence may not be present.

In an embodiment of the invention, the CAR comprises a transmembrane domain. In an embodiment of the invention, the transmembrane domain comprises CD8. The CD8 can comprise the CD8a (CD8 alpha) hinge and transmembrane domain. In a preferred embodiment, the CD8 is human. The CD8 may comprise less than the whole CD8. In embodiments of the invention, the CD8 may comprise the sequence as listed in Table 1 below.

In an embodiment of the invention, the CAR comprises an intracellular T cell signaling domain comprising 4-1BB (CD137), CD3 zeta ζ, or both. In a preferred embodiment, the CD3 zeta, 4-1BB, or both is/are human. 4-1BB transmits a potent costimulatory signal to T cells, promoting differentiation and enhancing long-term survival of T lymphocytes. CD3 ζ associates with TCRs to produce a signal and contains immunoreceptor tyrosine-based activation motifs (ITAMs). In an embodiment, the CAR lacks a 4-1BB domain. In another embodiment, the CAR comprises a CD28 domain. CD28 is a T cell marker important in T cell co-stimulation. The 4-1BB, CD28, CD3 zeta, or any of these may comprise less than the whole 4-1BB or CD3 zeta, respectively. In embodiments of the invention, the 4-1BB may comprise the sequence as listed in Table 1 below. In embodiments of the invention, the CD3 zeta may comprise the sequence as listed in Table 1 below.

In an embodiment of the invention, the CAR comprises a spacer. The spacer may be between any aforementioned domains. In an embodiment, the CAR comprises an IgG heavy chain constant domain (CH2CH3) spacer. In a further embodiment, the spacer can be between the scFv and the transmembrane domain. In a preferred embodiment, the sequence of the spacer, e.g., CH2CH3, is human. In embodiments of the invention, the spacer may comprise the sequence as listed in Table 1 below.

Embodiments of the invention comprise sequences as provided in Table 1 below.

TABLE 1

| Sequence | SEQ ID NO: | Segment | Notes |
|---|---|---|---|
| M | 3 | | start methionine |
| LLVTSLLLCELPHPAFLLIP | 4 | | signal peptide: from human GM-CSF |
| EVQLVQSGAEVKKPGSSVKVSCKAS | 5 | scFv | heavy chain: FR1 |
| GGTFSSYAIS | 6 | scFv | heavy chain: CDR1 |
| WVRQAPGQGLEWMG | 7 | scFv | heavy chain: FR2 |
| GIIPIFGTANYAQKFQG | 8 | scFv | heavy chain CDR2 |
| RVTITADKSTSTAYMELSSLRSEDTAVYYCAT | 9 | scFv | heavy chain: FR3 |
| FALFGFREQAFDI | 10 | scFv | heavy chain: J region (CDR3) |
| WGQGTTVTVSS | 11 | scFv | heavy chain: FR4 |
| GGGGSGGGGSGGGGS | 12 | scFv | linker |
| DIQMTQSPSSLSASVGDRVTITC | 13 | scFv | light chain: FR1 |
| RASQSISSYLN | 14 | scFv | light chain: CDR1 |
| WYQQKPGKAPKLLIY | 15 | scFv | light chain: FR2 |
| AASSLQS | 16 | scFv | light chain: CDR2 |
| GVPSRFSGSGSGTDFTLTISSLQPEDLATYYC | 17 | scFv | light chain: FR3 |
| QQSYSTPFT | 18 | scFv | light chain: J region (CDR3) |
| FGPGTKVDIK | 19 | scFv | light chain: FR4 |
| SG | 20 | | added amino acids due to vector design |
| LEDP | 21 | Spacer | |
| AEPKSPDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAK | 22 | Spacer | CH2 |
| GQPREPQVYTLPPSRDELTKNQVSLTCLVKGFYPSDIAVEWESNGQPENNYKTTPPVLDS | 23 | Spacer | CH3 |

TABLE 1-continued

| Sequence | SEQ ID NO: | Segment | Notes |
|---|---|---|---|
| DGSFFLYSKLTVDKSRWQQ GNVFSCSVMHEALHNHYTQ KSLSLSPGK | | | |
| KDPK | 24 | | Spacer |
| TTTPAPRPPTPAPTIASQPLSL RPEACRPAAGGAVHTRGLD FACD | 25 | CD8 | CD8α hinge |
| IYIWAPLAGTCGVLLLSLVIT LYC | 26 | CD8 | CD8α transmembrane domain |
| KRGRKKLLYIFKQPFMRPVQ TTQEEDGCSCRFPEEEEGGC EL | 27 | 4-1BB | intracellular domain |
| RVKFSRSADAPAYKQGQNQ LYNELNLGRREEYDVLDKR RGRDPEMGGKPRRKNPQEG LYNELQKDKMAEAYSEIGM KGERRRGKGHDGLYQGLST ATKDTYDALHMQALPPR | 28 | CD3ζ | intracellular domain |

Embodiments of the invention include the following sequences in Table 2 that comprise the sequences presented in Table 1 above.

TABLE 2

| Name | Short Form | Long Form |
|---|---|---|
| SEQ ID NO: Comprising Table 1 SEQ ID NOS: | 1 | 2 |
| | 3 | 3 |
| | 4 | 4 |
| | 5 | 5 |
| | 6 | 6 |
| | 7 | 7 |
| | 8 | 8 |
| | 9 | 9 |
| | 10 | 10 |
| | 11 | 11 |
| | 12 | 12 |
| | 13 | 13 |
| | 14 | 14 |
| | 15 | 15 |
| | 16 | 16 |
| | 17 | 17 |
| | 18 | 18 |
| | 19 | 19 |
| | 20 | 20 |
| | | 21 |
| | | 22 |
| | | 23 |
| | | 24 |
| | 25 | 25 |
| | 26 | 26 |
| | 27 | 27 |
| | 28 | 28 |

Embodiments of the invention include the following sequences in Table 3 that comprise the sequences presented in Table 1 above, where the signal peptide is not present.

TABLE 3

| Name | Short Form | Long Form |
|---|---|---|
| SEQ ID NO: Comprising Table 1 SEQ ID NOS: | 29 | 30 |
| | 5 | 5 |
| | 6 | 6 |
| | 7 | 7 |
| | 8 | 8 |
| | 9 | 9 |
| | 10 | 10 |
| | 11 | 11 |
| | 12 | 12 |
| | 13 | 13 |
| | 14 | 14 |
| | 15 | 15 |
| | 16 | 16 |
| | 17 | 17 |
| | 18 | 18 |
| | 19 | 19 |
| | 20 | 20 |
| | | 21 |
| | | 22 |
| | | 23 |
| | | 24 |
| | 25 | 25 |
| | 26 | 26 |
| | 27 | 27 |
| | 28 | 28 |

Included in the scope of the invention are functional portions of the inventive CARs described herein. The term "functional portion" when used in reference to a CAR refers to any part or fragment of the CAR of the invention, which part or fragment retains the biological activity of the CAR of which it is a part (the parent CAR). Functional portions encompass, for example, those parts of a CAR that retain the ability to recognize target cells, or detect, treat, or prevent a disease, to a similar extent, the same extent, or to a higher extent, as the parent CAR. In reference to the parent CAR, the functional portion can comprise, for instance, about 10%, 25%, 30%, 50%, 68%, 80%, 90%, 95%, or more, of the parent CAR.

The functional portion can comprise additional amino acids at the amino or carboxy terminus of the portion, or at both termini, which additional amino acids are not found in the amino acid sequence of the parent CAR. Desirably, the additional amino acids do not interfere with the biological function of the functional portion, e.g., recognize target cells, detect cancer, treat or prevent cancer, etc. More desirably, the additional amino acids enhance the biological activity, as compared to the biological activity of the parent CAR.

Included in the scope of the invention are functional variants of the inventive CARs described herein. The term "functional variant" as used herein refers to a CAR, polypeptide, or protein having substantial or significant sequence identity or similarity to a parent CAR, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to the parent CAR, the functional variant can, for instance, be at least about 30%, 50%, 75%, 80%, 90%, 98% or more identical in amino acid sequence to the parent CAR.

A functional variant can, for example, comprise the amino acid sequence of the parent CAR with at least one conservative amino acid substitution. Alternatively or additionally, the functional variants can comprise the amino acid sequence of the parent CAR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent CAR.

Amino acid substitutions of the inventive CARs are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gln, Ser, Thr, Tyr, etc.), an amino acid with a beta-branched side-chain substituted for another amino acid with a beta-branched side-chain (e.g., Ile, Thr, and Val), an amino acid with an aromatic side-chain substituted for another amino acid with an aromatic side chain (e.g., His, Phe, Trp, and Tyr), etc.

Also, amino acids may be added or removed from the sequence based on vector design. For example, SEQ ID NO: 20, added amino acids due to vector design, may be removed from the CARs as described herein, e.g., removed from the CAR sequences in Table 2, Table 3, or both.

The CAR can consist essentially of the specified amino acid sequence or sequences described herein, such that other components, e.g., other amino acids, do not materially change the biological activity of the functional variant.

The CARs of embodiments of the invention (including functional portions and functional variants) can be of any length, i.e., can comprise any number of amino acids, provided that the CARs (or functional portions or functional variants thereof) retain their biological activity, e.g., the ability to specifically bind to antigen, detect diseased cells in a mammal, or treat or prevent disease in a mammal, etc. For example, the CAR can be about 50 to about 5000 amino acids long, such as 50, 70, 75, 100, 125, 150, 175, 200, 300, 400, 500, 600, 700, 800, 900, 1000 or more amino acids in length.

The CARs of embodiments of the invention (including functional portions and functional variants of the invention) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The CARs of embodiments of the invention (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The CARs of embodiments of the invention (including functional portions and functional variants thereof) can be obtained by methods known in the art. The CARs may be made by any suitable method of making polypeptides or proteins. Suitable methods of de novo synthesizing polypeptides and proteins are described in references, such as Chan et al., *Fmoc Solid Phase Peptide Synthesis*, Oxford University Press, Oxford, United Kingdom, 2000; *Peptide and Protein Drug Analysis*, ed. Reid, R., Marcel Dekker, Inc., 2000; *Epitope Mapping*, ed. Westwood et al., Oxford University Press, Oxford, United Kingdom, 2001; and U.S. Pat. No. 5,449,752. Also, polypeptides and proteins can be recombinantly produced using the nucleic acids described herein using standard recombinant methods. See, for instance, Sambrook et al., *Molecular Cloning: A Laboratory Manual*, 3$^{rd}$ ed., Cold Spring Harbor Press, Cold Spring Harbor, NY 2001; and Ausubel et al., *Current Protocols in Molecular Biology*, Greene Publishing Associates and John Wiley & Sons, N Y, 1994. Further, some of the CARs of the invention (including functional portions and functional variants thereof) can be isolated and/or purified from a source, such as a plant, a bacterium, an insect, a mammal, e.g., a rat, a human, etc. Methods of isolation and purification are well-known in the art. Alternatively, the CARs described herein (including functional portions and functional variants thereof) can be commercially synthesized by companies. In this respect, the inventive CARs can be synthetic, recombinant, isolated, and/or purified.

An embodiment of the invention further provides an antibody, or antigen binding portion thereof, which specifically binds to an epitope of the CARs of the invention. The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for the functional portion of the inventive CAR.

Methods of testing antibodies for the ability to bind to any functional portion of the inventive CAR are known in the art and include any antibody-antigen binding assay, such as, for example, radioimmunoassay (RIA), ELISA, Western blot, immunoprecipitation, and competitive inhibition assays (see, e.g., Janeway et al., infra, U.S. Patent Application Publication No. 2002/0197266 A1, and U.S. Pat. No. 7,338,929).

Suitable methods of making antibodies are known in the art. For instance, standard hybridoma methods are described in, e.g., Köhler and Milstein, *Eur. J. Immunol.*, 5, 511-519 (1976), Harlow and Lane (eds.), *Antibodies: A Laboratory Manual*, CSH Press (1988), and C. A. Janeway et al. (eds.), *Immunobiology*, 5$^{th}$ Ed., Garland Publishing, New York, NY (2001)). Alternatively, other methods, such as EBV-hybridoma methods (Haskard and Archer, *J. Immunol. Methods*, 74(2), 361-67 (1984), and Roder et al., *Methods Enzymol.*, 121, 140-67 (1986)), and bacteriophage vector expression systems (see, e.g., Huse et al., Science, 246, 1275-81 (1989)) are known in the art. Further, methods of producing antibodies in non-human animals are described in, e.g., U.S. Pat. Nos. 5,545,806, 5,569,825, and 5,714,352, U.S. Patent Application Publication No. 2002/0197266 A1, and U.S. Pat. No. 7,338,929).

Phage display furthermore can be used to generate an antibody. In this regard, phage libraries encoding antigen-binding variable (V) domains of antibodies can be generated using standard molecular biology and recombinant DNA techniques (see, e.g., Sambrook et al., supra, and Ausubel et al., supra). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., *J. Mol. Biol.*, 235, 959-973 (1994).

An embodiment of the invention also provides antigen binding portions of any of the antibodies described herein. The antigen binding portion can be any portion that has at least one antigen binding site, such as Fab, F(ab')$_2$, dsFv, sFv, diabodies, and triabodies.

A single-chain variable region fragment antibody fragment can be generated using routine recombinant DNA technology techniques (see, e.g., Janeway et al., supra). Similarly, disulfide-stabilized variable region fragments can be prepared by recombinant DNA technology (see, e.g., Reiter et al., *Protein Engineering*, 7, 697-704 (1994)). Antibody fragments of the invention, however, are not limited to these exemplary types of antibody fragments.

Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

Further provided by an embodiment of the invention is a nucleic acid comprising a nucleotide sequence encoding any of the CARs described herein (including functional portions and functional variants thereof). The nucleic acids of the invention may comprise a nucleotide sequence encoding any of the leader sequences, antigen binding domains, transmembrane domains, and/or intracellular T cell signaling domains described herein.

In some embodiments, the nucleotide sequence may be codon-optimized. Without being bound to a particular theory, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency.

In an embodiment of the invention, the nucleic acid may comprise a codon-optimized nucleotide sequence that encodes the antigen binding domain of the inventive CAR. In another embodiment of the invention, the nucleic acid may comprise a codon-optimized nucleotide sequence that encodes any of the CARs described herein (including functional portions and functional variants thereof).

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions.

The nucleic acids of an embodiment of the invention may be recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Sambrook et al., supra. The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Integrated DNA Technologies (Coralville, IA, USA).

The nucleic acid can comprise any isolated or purified nucleotide sequence which encodes any of the CARs or functional portions or functional variants thereof. Alternatively, the nucleotide sequence can comprise a nucleotide sequence which is degenerate to any of the sequences or a combination of degenerate sequences.

An embodiment of the invention also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarily are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive CARs. It is generally appreciated that conditions can be rendered more stringent by the addition of increasing amounts of formamide.

The invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

In an embodiment, the nucleic acids of the invention can be incorporated into a recombinant expression vector. In this regard, an embodiment of the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector.

In an embodiment, the recombinant expression vector of the invention can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences, Glen Burnie, MD), the pBluescript series (Stratagene, LaJolla, CA), the pET series (Novagen, Madison, WI), the pGEX series (Pharmacia Biotech, Uppsala, Sweden), and the pEX series (Clontech, Palo Alto, CA). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM, and pMAMneo (Clontech). The recombinant expression vector may be a viral vector, e.g., a retroviral vector or a lentiviral vector.

A number of transfection techniques are generally known in the art (see, e.g., Graham et al., *Virology*, 52: 456-467 (1973); Sambrook et al., supra; Davis et al., *Basic Methods in Molecular Biology*, Elsevier (1986); and Chu et al., *Gene*, 13: 97 (1981). Transfection methods include calcium phosphate co-precipitation (see, e.g., Graham et al., supra), direct micro injection into cultured cells (see, e.g., Capecchi, *Cell*, 22: 479-488 (1980)), electroporation (see, e.g., Shigekawa et al., *BioTechniques*, 6: 742-751 (1988)), liposome mediated gene transfer (see, e.g., Mannino et al., *BioTechniques*, 6: 682-690 (1988)), lipid mediated transduction (see, e.g., Felgner et al., *Proc. Natl. Acad. Sci. USA*, 84: 7413-7417

(1987)), and nucleic acid delivery using high velocity microprojectiles (see, e.g., Klein et al., *Nature,* 327: 70-73 (1987)).

In an embodiment, the recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColEl, 2 μplasmid, λ, SV40, bovine papilloma virus, and the like.

The recombinant expression vector may comprise regulatory sequences, such as transcription and translation initiation and termination codons, which are specific to the type of host cell (e.g., bacterium, fungus, plant, or animal) into which the vector is to be introduced, as appropriate, and taking into consideration whether the vector is DNA- or RNA-based. The recombinant expression vector may comprise restriction sites to facilitate cloning.

The recombinant expression vector can include one or more marker genes, which allow for selection of transformed or transfected host cells. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the CAR (including functional portions and functional variants thereof), or to the nucleotide sequence which is complementary to or which hybridizes to the nucleotide sequence encoding the CAR. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, *Suicide Gene Therapy: Methods and Reviews*, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

Included in the scope of the invention are conjugates, e.g., bioconjugates, comprising any of the inventive CARs (including any of the functional portions or variants thereof), nucleic acids, recombinant expression vectors, host cells, populations of host cells, or antibodies, or antigen binding portions thereof. Conjugates, as well as methods of synthesizing conjugates in general, are known in the art (See, for instance, Hudecz, F., *Methods Mol. Biol.* 298: 209-223 (2005) and Kirin et al., *Inorg Chem.* 44(15): 5405-5415 (2005)). CARs of the invention may be conjugated to, e.g., toxins that are toxic to cancer cells.

An embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α *E. coli* cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5α cell. For purposes of producing a recombinant CAR, the host cell may be a mammalian cell. The host cell may be a human cell. While the host cell can be of any cell type, can originate from any type of tissue, and can be of any developmental stage, the host cell may be a peripheral blood lymphocyte (PBL) or a peripheral blood mononuclear cell (PBMC). The host cell may be a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, CD4+/CD8+ double positive T cells, CD4+ helper T cells, e.g., $Th_1$ and $Th_2$ cells, CD8+ T cells (e.g., cytotoxic T cells), tumor infiltrating cells, memory T cells, naïve T cells, and the like. The T cell may be a CD8+ T cell or a CD4+ T cell.

In an embodiment, the CARs as described herein can be used in suitable non-T cells. Such cells are those with an immune-effector function, such as, for example, NK cells, and T-like cells generated from pluripotent stem cells.

Also provided by an embodiment of the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

CARs (including functional portions and variants thereof), nucleic acids, recombinant expression vectors, host cells (including populations thereof), and antibodies (including antigen binding portions thereof), all of which are collectively referred to as "inventive CAR materials" hereinafter, can be isolated and/or purified. The term "isolated" as used herein means having been removed from its natural environment. The term "purified" or "isolated" does not require absolute purity or isolation; rather, it is intended as a relative term. Thus, for example, a purified (or isolated) host cell preparation is one in which the host cell is more pure than cells in their natural environment within the body. Such host cells may be produced, for example, by standard purification techniques. In some embodiments, a preparation of a host cell is purified such that the host cell represents at least about 50%, for example at least about 70%, of the total cell content of the preparation. For example, the purity can be at least about 50%, can be greater than about 60%, about 70% or about 80%, or can be about 100%.

The inventive CAR materials can be formulated into a composition, such as a pharmaceutical composition. In this regard, an embodiment of the invention provides a pharmaceutical composition comprising any of the CARs, functional portions, functional variants, nucleic acids, expression vectors, host cells (including populations thereof), and antibodies (including antigen binding portions thereof), and a pharmaceutically acceptable carrier. The inventive pharmaceutical compositions containing any of the inventive CAR materials can comprise more than one inventive CAR material, e.g., a CAR and a nucleic acid, or two or more different CARs. Alternatively, the pharmaceutical composition can comprise an inventive CAR material in combination with other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In a preferred embodiment, the pharmaceutical composition comprises the inventive host cell or populations thereof.

The inventive CAR materials can be provided in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

With respect to pharmaceutical compositions, the pharmaceutically acceptable carrier can be any of those conventionally used and is limited only by chemico-physical considerations, such as solubility and lack of reactivity with the active agent(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular inventive CAR material, as well as by the particular method used to administer the inventive CAR material. Accordingly, there are a variety of suitable formulations of the pharmaceutical composition of the invention. Preservatives may be used. Suitable preservatives may include, for example, methylparaben, propylparaben, sodium benzoate, and benzalkonium chloride. A mixture of two or more preservatives optionally may be used. The preservative or mixtures thereof are typically present in an amount of about 0.0001% to about 2% by weight of the total composition.

Suitable buffering agents may include, for example, citric acid, sodium citrate, phosphoric acid, potassium phosphate, and various other acids and salts. A mixture of two or more buffering agents optionally may be used. The buffering agent or mixtures thereof are typically present in an amount of about 0.001% to about 4% by weight of the total composition.

The concentration of inventive CAR material in the pharmaceutical formulations can vary, e.g., from less than about 1%, usually at or at least about 10%, to as much as about 20% to about 50% or more by weight, and can be selected primarily by fluid volumes, and viscosities, in accordance with the particular mode of administration selected.

Methods for preparing administrable (e.g., parenterally administrable) compositions are known or apparent to those skilled in the art and are described in more detail in, for example, *Remington: The Science and Practice of Pharmacy*, Lippincott Williams & Wilkins; 21st ed. (May 1, 2005).

The following formulations for oral, aerosol, parenteral (e.g., subcutaneous, intravenous, intraarterial, intramuscular, intradermal, interperitoneal, and intrathecal), and topical administration are merely exemplary and are in no way limiting. More than one route can be used to administer the inventive CAR materials, and in certain instances, a particular route can provide a more immediate and more effective response than another route.

Formulations suitable for oral administration can comprise or consist of (a) liquid solutions, such as an effective amount of the inventive CAR material dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard or softshelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the inventive CAR material in a flavor, usually sucrose and acacia or tragacanth, as well as pastilles comprising the inventive CAR material in an inert base, such as gelatin and glycerin, or sucrose and acacia, emulsions, gels, and the like containing, in addition to, such excipients as are known in the art.

Formulations suitable for parenteral administration include aqueous and nonaqueous isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The inventive CAR material can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1,3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain, for example, from about 0.5% to about 25% by weight of the inventive CAR material in solution. Preservatives and buffers may be used. In order to minimize or eliminate irritation at the site of injection, such compositions may contain one or more nonionic surfactants having, for example, a hydrophile-lipophile balance (HLB) of from about 12 to about 17. The quantity of surfactant in such formulations will typically range, for example, from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Injectable formulations are in accordance with an embodiment of the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, PA, Banker and Chalmers, eds., pages 238-250 (1982), and *ASHP Handbook on Injectable Drugs*, Toissel, 4th ed., pages 622-630 (1986)).

Topical formulations, including those that are useful for transdermal drug release, are well known to those of skill in the art and are suitable in the context of embodiments of the invention for application to skin. The inventive CAR material, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

An "effective amount" or "an amount effective to treat" refers to a dose that is adequate to prevent or treat cancer in an individual. Amounts effective for a therapeutic or prophylactic use will depend on, for example, the stage and severity of the disease or disorder being treated, the age, weight, and general state of health of the patient, and the judgment of the prescribing physician. The size of the dose will also be determined by the active selected, method of administration, timing and frequency of administration, the existence, nature, and extent of any adverse side-effects that might accompany the administration of a particular active, and the desired physiological effect. It will be appreciated by one of skill in the art that various diseases or disorders could require prolonged treatment involving multiple administrations, perhaps using the inventive CAR materials in each or various rounds of administration. By way of example and not intending to limit the invention, the dose of the inventive CAR material can be about 0.001 to about 1000 mg/kg body weight of the subject being treated/day, from about 0.01 to about 10 mg/kg body weight/day, about 0.01 mg to about 1 mg/kg body weight/day. In an embodiment of the invention, the dose may be from about $1\times10^4$ to about $1\times10^8$ cells expressing the inventive CAR material per kg body weight. When the inventive CAR material is a host cell, an exemplary dose of host cells may be a minimum of one million cells (1 mg cells/dose). When the inventive CAR material is a nucleic acid packaged in a virus, an exemplary dose of virus may be 1 ng/dose.

For purposes of the invention, the amount or dose of the inventive CAR material administered should be sufficient to effect a therapeutic or prophylactic response in the subject or animal over a reasonable time frame. For example, the dose of the inventive CAR material should be sufficient to bind to antigen, or detect, treat or prevent disease in a period of from about 2 hours or longer, e.g., about 12 to about 24 or more hours, from the time of administration. In certain embodiments, the time period could be even longer. The dose will be determined by the efficacy of the particular inventive CAR material and the condition of the animal (e.g., human), as well as the body weight of the animal (e.g., human) to be treated.

For purposes of the invention, an assay, which comprises, for example, comparing the extent to which target cells are lysed and/or IFN-γ is secreted by T cells expressing the inventive CAR upon administration of a given dose of such T cells to a mammal, among a set of mammals of which is each given a different dose of the T cells, could be used to determine a starting dose to be administered to a mammal. The extent to which target cells are lysed and/or IFN-γ is secreted upon administration of a certain dose can be assayed by methods known in the art.

In addition to the aforedescribed pharmaceutical compositions, the inventive CAR materials can be formulated as inclusion complexes, such as cyclodextrin inclusion complexes, or liposomes. Liposomes can serve to target the inventive CAR materials to a particular tissue. Liposomes also can be used to increase the half-life of the inventive CAR materials. Many methods are available for preparing liposomes, as described in, for example, Szoka et al., *Ann. Rev. Biophys. Bioeng.*, 9, 467 (1980) and U.S. Pat. Nos. 4,235,871, 4,501,728, 4,837,028, and 5,019,369.

The delivery systems useful in the context of embodiments of the invention may include time-released, delayed release, and sustained release delivery systems such that the delivery of the inventive composition occurs prior to, and with sufficient time to cause, sensitization of the site to be treated. The inventive composition can be used in conjunction with other therapeutic agents or therapies. Such systems can avoid repeated administrations of the inventive composition, thereby increasing convenience to the subject and the physician, and may be particularly suitable for certain composition embodiments of the invention.

Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the active composition is contained in a form within a matrix such as those described in U.S. Pat. Nos. 4,452,775, 4,667,014, 4,748,034, and 5,239,660 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

One of ordinary skill in the art will readily appreciate that the inventive CAR materials of the invention can be modified in any number of ways, such that the therapeutic or prophylactic efficacy of the inventive CAR materials is increased through the modification. For instance, the inventive CAR materials can be conjugated either directly or indirectly through a linking moiety to a targeting moiety. The practice of conjugating compounds, e.g., inventive CAR materials, to targeting moieties is known in the art. See, for instance, Wadwa et al., *J. Drug Targeting* 3: 111 (1995) and U.S. Pat. No. 5,087,616.

The inventive CAR materials can be modified into a depot form, such that the manner in which the inventive CAR materials is released into the body to which it is administered is controlled with respect to time and location within the body (see, for example, U.S. Pat. No. 4,450,150). Depot forms of inventive CAR materials can be, for example, an implantable composition comprising the inventive CAR materials and a porous or non-porous material, such as a polymer, wherein the inventive CAR materials are encapsulated by or diffused throughout the material and/or degradation of the non-porous material. The depot is then implanted into the desired location within the body and the inventive CAR materials are released from the implant at a predetermined rate.

When the inventive CAR materials are administered with one or more additional therapeutic agents, one or more additional therapeutic agents can be coadministered to the mammal. By "coadministering" is meant administering one or more additional therapeutic agents and the inventive CAR materials sufficiently close in time such that the inventive CAR materials can enhance the effect of one or more additional therapeutic agents, or vice versa. In this regard, the inventive CAR materials can be administered first and the one or more additional therapeutic agents can be administered second, or vice versa. Alternatively, the inventive CAR materials and the one or more additional therapeutic agents can be administered simultaneously.

An exemplary therapeutic agent that can be co-administered with the CAR materials is a T cell active cytokine, such as IL-2. It is believed that IL-2 enhances the therapeutic effect of the inventive CAR materials. Without being bound by a particular theory or mechanism, it is believed that IL-2 enhances therapy by enhancing the in vivo expansion of the numbers and/or effector function of cells expressing the inventive CARs. Other exemplary cytokines include IL-7 and IL-15. For purposes of the inventive methods, wherein host cells or populations of cells are administered to the mammal, the cells can be cells that are allogeneic or autologous to the mammal.

It is contemplated that the inventive CARs materials can be used in methods of treating or preventing a disease in a mammal. Without being bound to a particular theory or mechanism, the inventive CARs have biological activity, e.g., ability to recognize antigen, e.g., FLT3, such that the CAR when expressed by a cell is able to mediate an immune response against the cell expressing the antigen, e.g., FLT3, for which the CAR is specific. In this regard, an embodiment of the invention provides a method of treating or preventing cancer in a mammal, comprising administering to the mammal the CARs, the nucleic acids, the recombinant expression vectors, the host cells, the population of cells, the antibodies and/or the antigen binding portions thereof, and/or the pharmaceutical compositions of the invention in an amount effective to treat or prevent cancer in the mammal.

An embodiment of the invention further comprises lymphodepleting the mammal prior to administering the inventive CAR materials. Examples of lymphodepletion include, but may not be limited to, nonmyeloablative lymphodepleting chemotherapy, myeloablative lymphodepleting chemotherapy, total body irradiation, etc.

For purposes of the inventive methods, wherein host cells or populations of cells are administered, the cells can be cells that are allogeneic or autologous to the mammal. Preferably, the cells are autologous to the mammal.

The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human.

With respect to the inventive methods, the cancer can be any cancer, including any of acute lymphocytic cancer, acute myeloid leukemia (AML), alveolar rhabdomyosarcoma, bladder cancer (e.g., bladder carcinoma), bone cancer, brain cancer (e.g., medulloblastoma), breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, head and neck cancer (e.g., head and neck squamous cell carcinoma), Hodgkin lymphoma, hypopharynx cancer, kidney cancer, larynx cancer, leukemia, liquid tumors, liver cancer, lung cancer (e.g., non-small cell lung carcinoma and lung adenocarcinoma), lymphoma, mesothelioma, mastocytoma, melanoma, multiple myeloma, nasopharynx cancer, non-Hodgkin lymphoma, B-chronic lymphocytic leukemia, hairy cell leukemia, acute lymphocytic leukemia (ALL), and Burkitt's lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, synovial sarcoma, gastric cancer, testicular cancer, thyroid cancer, and ureter cancer. Preferably, the cancer is characterized by the expression of FLT3.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount or any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

Another embodiment of the invention provides a method of detecting the presence of cancer in a mammal, comprising: (a) contacting a sample comprising one or more cells from the mammal with the CARs, the nucleic acids, the recombinant expression vectors, the host cells, the population of cells, the antibodies, and/or the antigen binding portions thereof, or the pharmaceutical compositions of the invention, thereby forming a complex, (b) and detecting the complex, wherein detection of the complex is indicative of the presence of cancer in the mammal.

Another embodiment of the invention includes a method of determining whether a subject with a proliferative disorder is a candidate for treatment with a chimeric antigen receptor comprising an antigen binding domain specific for FLT3, the method comprising measuring FLT3 expression levels in a biological sample from the subject; and determining if the FLT3 expression levels of the biological sample are increased compared to a sample from a control subject without the proliferative disorder.

The sample may be obtained by any suitable method, e.g., biopsy or necropsy. A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from a certain condition or disease-state. The condition or disease may be, e.g., cancer.

With respect to an embodiment of the inventive method of detecting the presence of a proliferative disorder, e.g., cancer, in a mammal, the sample comprising cells of the mammal can be a sample comprising whole cells, lysates thereof, or a fraction of the whole cell lysates, e.g., a nuclear or cytoplasmic fraction, a whole protein fraction, or a nucleic acid fraction. If the sample comprises whole cells, the cells can be any cells of the mammal, e.g., the cells of any organ or tissue, including blood cells or endothelial cells.

The contacting can take place in vitro or in vivo with respect to the mammal. Preferably, the contacting is in vitro.

Also, detection of the complex can occur through any number of ways known in the art. For instance, the inventive CARs, polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

Methods of testing a CAR for the ability to recognize target cells and for antigen specificity are known in the art. For instance, Clay et al., J. Immunol., 163: 507-513 (1999), teaches methods of measuring the release of cytokines (e.g., interferon-γ, granulocyte/monocyte colony stimulating factor (GM-CSF), tumor necrosis factor α (TNF-α) or interleukin 2 (IL-2)). In addition, CAR function can be evaluated by measurement of cellular cytotoxicity, as described in Zhao et al., J. Immunol., 174: 4415-4423 (2005).

Another embodiment of the invention provides the use of the CARs, nucleic acids, recombinant expression vectors, host cells, populations of cells, antibodies, or antigen binding portions thereof, and/or pharmaceutical compositions of the invention, for the treatment or prevention of a proliferative disorder, e.g., cancer, in a mammal. The cancer may be any of the cancers described herein. Preferably, the cancer is pre-B cell precursor acute lymphoblastic leukemia or acute myeloid leukemia.

It shall be noted that the preceding are merely examples of embodiments. Other exemplary embodiments are apparent from the entirety of the description herein. It will also be understood by one of ordinary skill in the art that each of these embodiments may be used in various combinations with the other embodiments provided herein.

The following includes certain aspects of the invention.

1. A chimeric antigen receptor (CAR) comprising an antigen binding domain specific for FLT3, a transmembrane domain, and an intracellular T cell signaling domain.

2. The CAR according to aspect 1, wherein the antigen binding domain comprises the light chain variable region comprising the sequences of SEQ ID NOS: 13-19.

3. The CAR according to aspect 1 or 2, wherein the antigen binding domain comprises the heavy chain variable region comprising the sequences of SEQ ID NOS: 5-11.

4. The CAR according to any one of aspects 1-3, wherein the antigen binding domain comprises the linker sequence of SEQ ID NO: 12.

5. The CAR according to any one of aspects 1-4, wherein the antigen binding domain comprises SEQ ID NOS: 5-19.

6. The CAR according to any one of aspects 1-5, wherein the transmembrane domain comprises a CD8 amino acid sequence.

7. The CAR according to any one of aspects 1-6, wherein the transmembrane domain comprises CD8 amino acid sequence comprising the CD8a hinge sequence of SEQ ID NO: 25 and the transmembrane domain of sequence SEQ ID NO: 26.

8. The CAR according to any one of aspects 1-7, wherein the intracellular T cell signaling domain comprises 4-1BB, CD3 zeta, or both.

9. The CAR according to any one of aspects 1-8, wherein the intracellular T cell signaling domain comprises the 4-1BB amino acid sequence of SEQ ID NO: 27.

10. The CAR according to any one of aspects 1-9, wherein the intracellular T cell signaling domain comprises the CD3 zeta amino acid sequence of SEQ ID NO: 28.

11. The CAR according to any one of aspects 1-10, wherein the CAR further comprises the spacer comprising SEQ ID NOS: 21-24.

12. The CAR according to aspect 1, wherein the CAR comprises any one of the sequence of SEQ ID NOS: 1, 2, 29, or 30.

13. A nucleic acid comprising a nucleotide sequence encoding the CAR according to any one of aspects 1-12.

14. The nucleic acid according to aspect 13, wherein the nucleotide sequence is codon-optimized.

15. A recombinant expression vector comprising the nucleic acid according to aspect 13 or 14.

16. The recombinant expression vector according to aspect 15, wherein the recombinant expression vector is a lentiviral vector.

17. An isolated host cell comprising the recombinant expression vector of aspect 15 or 16.

18. A population of cells comprising at least one host cell of aspect 17.

19. An antibody, or antigen binding portion thereof, which specifically binds to a CAR according to any one of aspects 1-12.

20. A pharmaceutical composition comprising the CAR any one of aspects 1-12, the nucleic acid of aspect 13 or 14, the recombinant expression vector of aspect 15 or 16, the host cell of aspect 17, the population of cells of aspect 18, or the antibody, or antigen binding portion thereof of aspect 19, and a pharmaceutically acceptable carrier.

21. A method of detecting the presence of cancer, comprising:
  (a) contacting a sample comprising one or more cells with the CAR any one of aspects 1-12, the nucleic acid of aspect 13 or 14, the recombinant expression vector of aspect 15 or 16, the host cell of aspect 17, the population of cells of aspect 18, the antibody, or antigen binding portion thereof, of aspect 19, or the pharmaceutical composition of aspect 20, thereby forming a complex, and
  (b) detecting the complex, wherein detection of the complex is indicative of the presence of cancer.

22. The method of aspect 21, wherein the cancer is pre-B cell precursor acute lymphoblastic leukemia or acute myeloid leukemia.

23. The CAR of any one of aspects 1-12, the nucleic acid of aspect 13 or 14, the recombinant expression vector of aspect 15 or 16, the host cell of aspect 17, the population of cells of aspect 18, the antibody, or antigen binding portion thereof of aspect 19, or the pharmaceutical composition of aspect 20, for use in the treatment or prevention of cancer in a mammal.

24. The CAR, nucleic acid, recombinant expression vector, host cell, population of cells, antibody, or antigen binding portion thereof, or pharmaceutical composition of aspect 23, wherein the cancer is pre-B cell precursor acute lymphoblastic leukemia or acute myeloid leukemia.

25. A method of determining whether a subject with a proliferative disorder is a candidate for treatment with a chimeric antigen receptor comprising an antigen binding domain specific for FLT3, the method comprising: measuring FLT3 expression levels in a biological sample from the subject; and determining if the FLT3 expression levels of the biological sample are increased compared to a sample from a control subject without the proliferative disorder.

The following examples further illustrate the invention but, of course, should not be construed as in any way limiting its scope.

Example 1

This example demonstrates that FLT3 is expressed on acute lymphoblastic and acute myeloid leukemia cell lines.

The number of FLT3 receptors per cell was quantified on various acute lymphoblastic [NALM6 (DSMZ no. ACC 128), HB11; 19 (Horsley et al., Genes Chromosomes Cancer, 45:554-564 (2006)), KOPN-8 (DSMZ no. ACC 552), SEM (DSMZ no. ACC 546)] and acute myeloid [MOLM13 (DSMZ no. ACC 554), MOLM14 (DSMZ no. ACC 577), MV4; 11 (DSMZ no. ACC 102), THP-1 (DSMZ no. ACC 16)] leukemia cell lines by flow cytometry using BD Quantibrite beads as per manufacturer's protocol (BD Biosciences; San Jose, CA, USA) and Phycoerythrin (PE) labeled anti human CD135 (FLT3) antibody (eBioscience; San Diego, CA, USA; clone BV10A4H2). KOPN-8 is a cell line derived from a patient with infant ALL. DSMZ is the Leibniz-Institute DSMZ-German Collection of Microorganisms and Cell Cultures (Braunschweig, Germany).

All cell lines were cultured using RPMI 1640 (Invitrogen; Carlsbad, CA, USA) media supplemented with 10% heat inactivated fetal bovine serum (Omega Scientific; Tarzana, CA, USA), 100 U/mL penicillin, 100 mg/mL streptomycin, and 2 mM L-glutamine (Invitrogen). Labeled samples were analyzed by flow cytometry on a BD LSR Fortessa (BD Biosciences) and data analysis was performed using FlowJo software (FlowJo LLC, Ashland, OR, USA) and GraphPad Prism (GraphPad Software; La Jolla, CA, USA). FIG. 1 shows the results.

Example 2

This example demonstrates the production of a CAR in accordance with embodiments of the invention.

Figure 2:
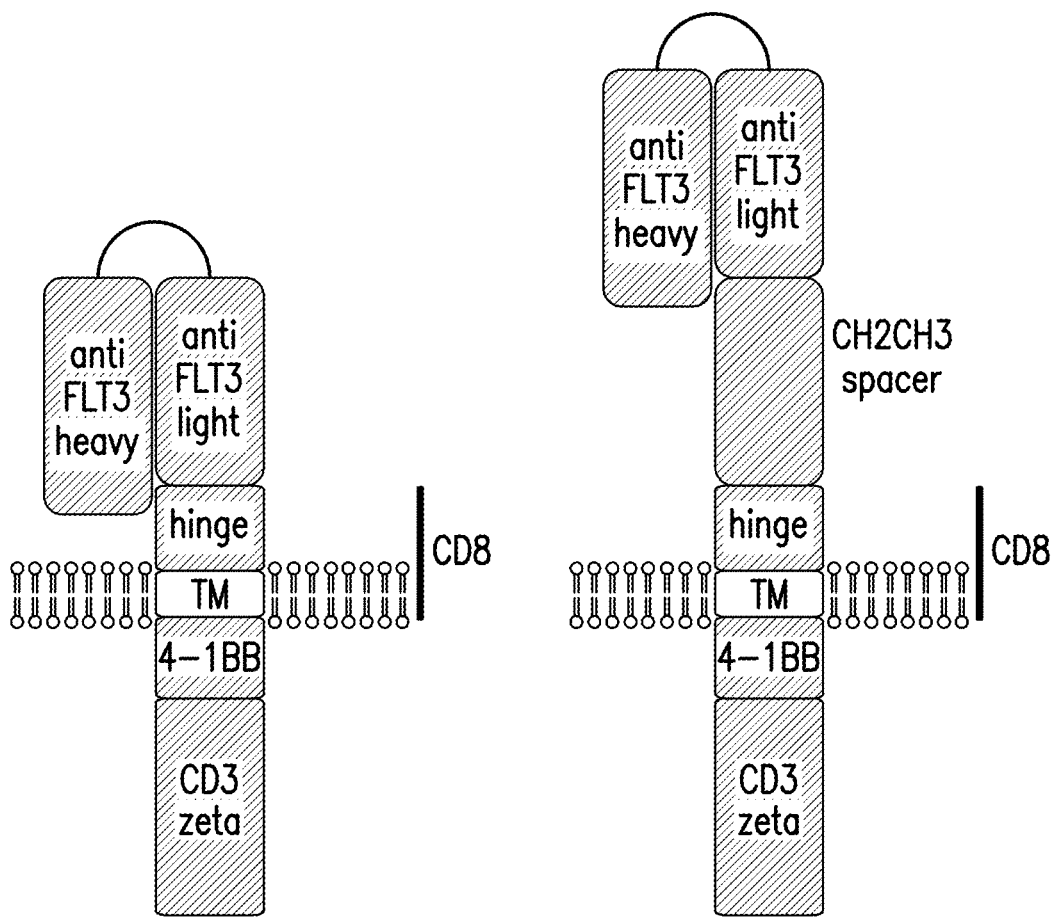
FIG. 2 is a diagram of CARs in accordance with embodiments of the invention.

The amino acid sequence encoding the FLT3 scFv was converted to DNA sequence and codon optimized and synthesized using GeneArt™ gene synthesis (ThermoFisher Scientific; Waltham, MA, USA) with kozak sequence, membrane localization leader sequence from human granulocyte macrophage colony stimulating factor (GM-CSF), 5' NheI restriction site, and 3' BspEI restriction site. The FLT3 scFV sequence was then subcloned from the provided GeneArt™ vector and moved using standard molecular cloning techniques to the third generation lentiviral plasmid pELNS-19BBzeta which contains the CD8 hinge and transmembrane, 4-1BB signaling domain, and the CD3zeta domain using the NheI and BspEI cloning sites. FIG. 2 shows a diagram of the CAR (left side of figure). The CAR was SEQ ID NO: 1/29. The leader sequence is initially encoded and enhances trafficking to the cell surface; it is likely to be cleaved off in the mature form.

Lentiviral supernatant generation: 293T cells (ATCC; Manassas, VA, USA; ATCC no. CRL-3216) were transiently transfected with third generation lentiviral plasmids to generate viral supernatant. 293T cells were plated in poly-D lysine coated 15 cm tissue culture plates (Corning; Tewksbury, MA, USA) in DMEM supplemented with 10% heat inactivated fetal bovine serum (Omega Scientific), 100 U/mL penicillin, 100 mg/mL streptomycin, and 2 mM L-glutamine (Invitrogen) and allowed to adhere for 16 hours. The following day, GFP or FLT3 CAR containing plasmids, pMDLg/pRRE and pRSV-Rev packaging, and pMD-G envelope plasmids were lipid transfected into the 293T cells using Lipofectamine 3000 (Invitrogen) as per manufacturer's protocol. Media containing the transfection mixture was discarded and replaced with fresh media 4-6 hours after transfection mixture was added. Viral supernatant was collected at 24, 48, and 72 hours post transfection, centrifuged at 1200 rpm for 6 minutes to remove cells, and stored at −80° C. until use.

T cell source: Human elutriated lymphocytes from normal donors were used as a source of T cells for experiments and were obtained from the Department of Transfusion Medicine at the NIH Clinical Center under an NIH IRB approved protocol after informed consent in accordance with the Declaration of Helsinki. Donor lymphocytes were cleared of red blood cells using Lymphocyte Separation Medium (Lonza; Basel, Switzerland) as per manufacturer's protocol and cryopreserved in heat inactivated fetal bovine serum (FBS; Omega Scientific) with 10% Dimethyl sulfoxide (DMSO; Sigma Aldrich; St Louis, MO, USA) and stored in liquid nitrogen.

T cell transduction: Elutriated lymphocytes were thawed and cultured in T cell expansion media (TCEM) which consists of AIM-V media (Invitrogen) supplemented with 5% heat inactivated FBS (Omega Scientific), 100 U/mL penicillin, 100 mg/mL streptomycin, 15 mM HEPES, and 2 mM L-glutamine (Invitrogen) and 40 IU/ml IL-2 with Dynabeads Human T-Expander CD3/CD28 beads (Invitrogen) at a 3:1 bead to cell ratio. Cells were cultured for 2 days prior to transduction with viral supernatant. Two million T cells were plated per well of a 6 well plate in 1 ml TCEM+3 ml viral supernatant with a final concentration of 40 IU/mL of IL-2 and 10 mg/mL of protamine sulfate. The 6-well plates of T cells were centrifuged at 872 g for 2 hours at 32° C. and then incubated at 37° C. overnight. The following day, Dynabeads were removed using a magnetic rack and the T cells were cultured in fresh TCEM with 300 IU/mL IL2 at 500,000 cells/mL. T cells were cultured until day 9 in TCEM with 300 IU/mL of IL-2 maintaining the cells below 1 million/mL and the T cell transduction was determined by flow cytometry.

Example 3

This example demonstrates FLT3 CAR T cell transduction in accordance with embodiments of the invention.

Figure 3:
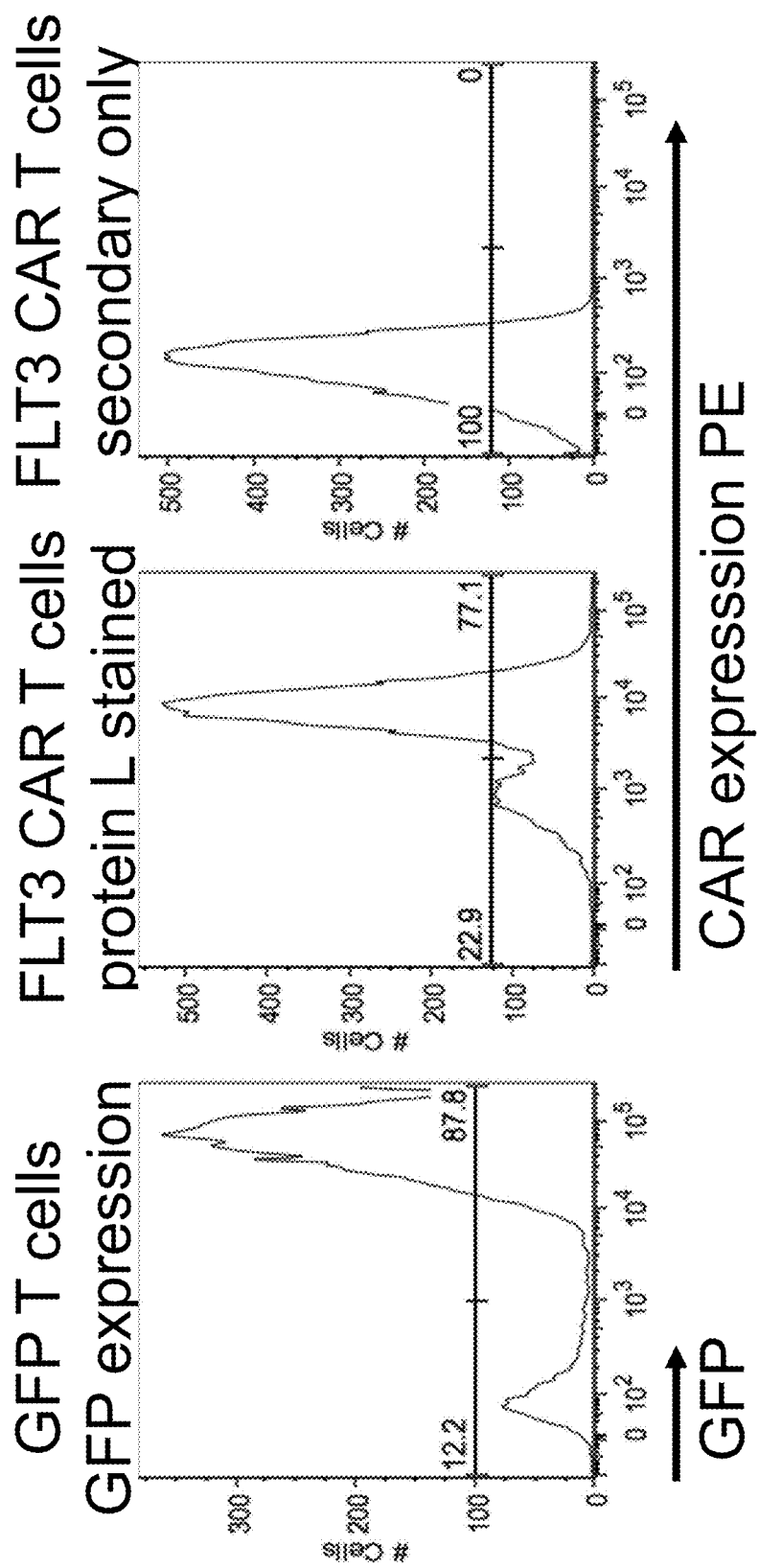
FIG. 3 shows flow cytometry graphs of FLT3 CAR T cell transduction, in accordance with embodiments of the invention.
Figure 4:
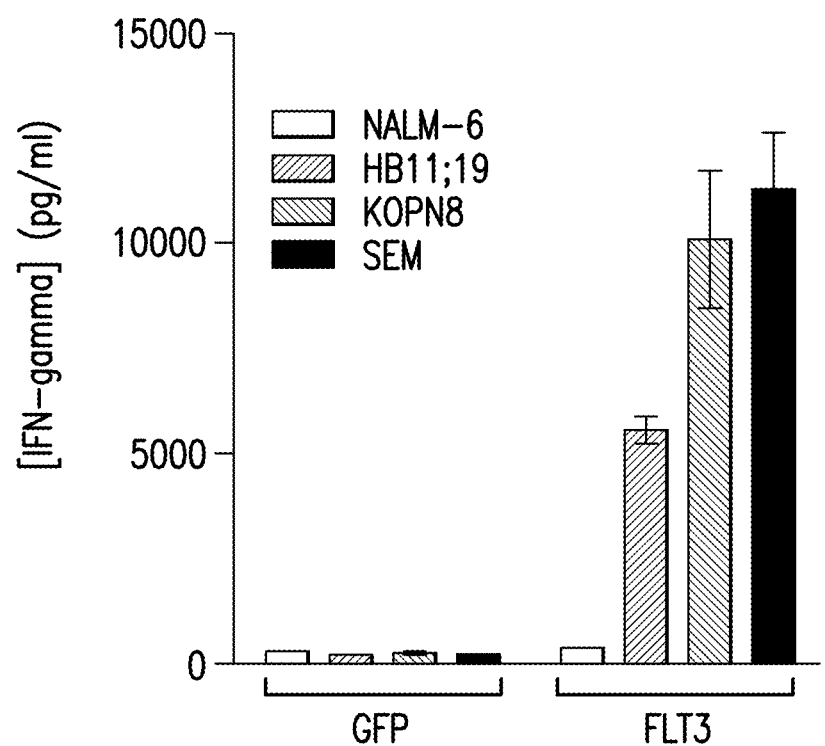
FIG. 4 is a bar graph showing that T cells expressing FLT3-targeting chimeric antigen receptors secrete high levels of interferon-gamma when co-cultured with FLT3-expressing ALL cell lines, in accordance with embodiments of the invention.
Figure 5:
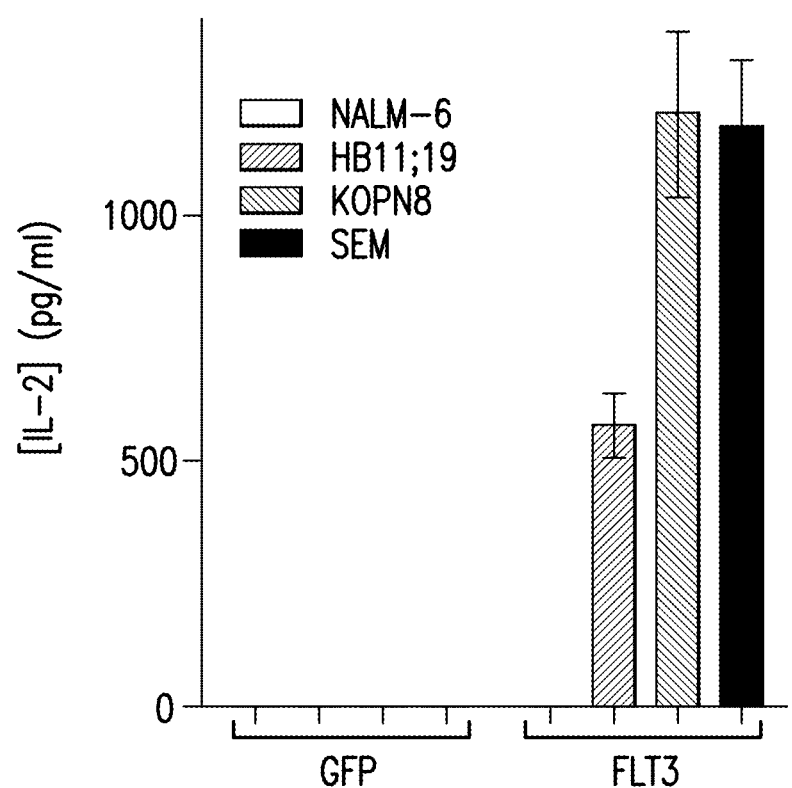
FIG. 5 is a bar graph showing that T cells expressing FLT3 targeting chimeric antigen receptors secrete high levels of interleukin-2 when co-cultured with FLT3-expressing ALL cell lines, in accordance with embodiments of the invention.
Figure 6:
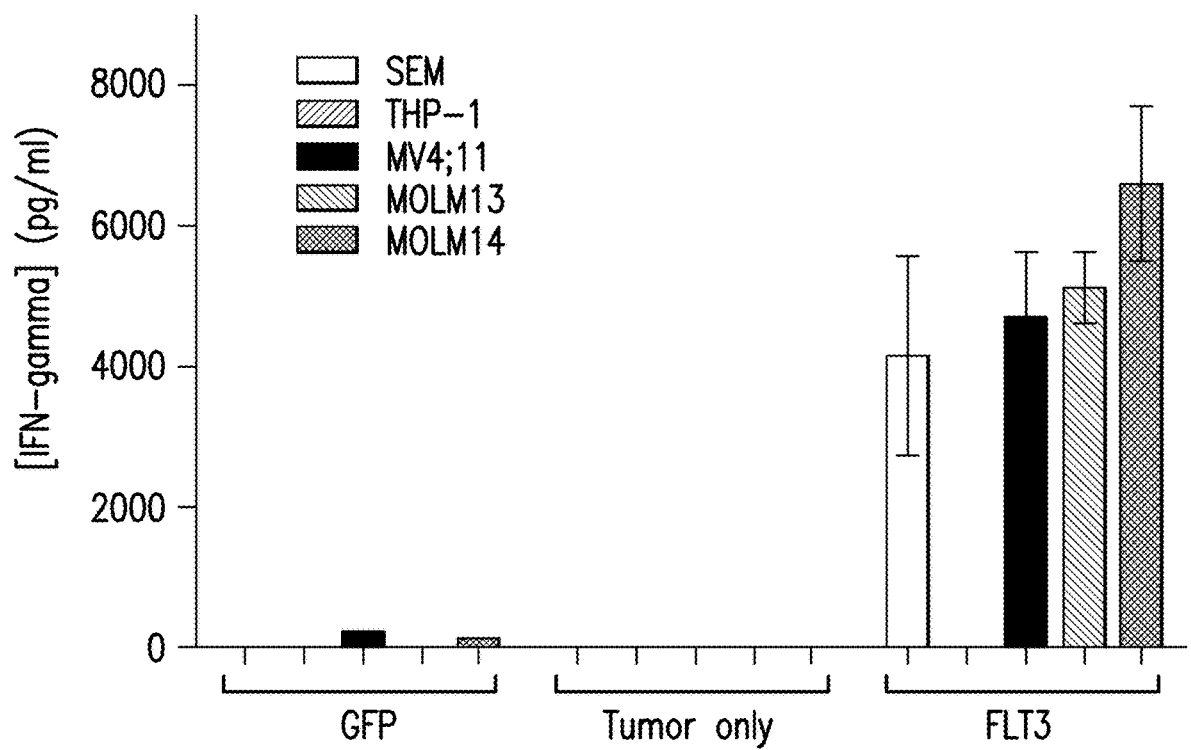
FIG. 6 is a bar graph showing that T cells expressing a FLT3 targeting chimeric antigen receptor secrete high levels of interferon-gamma when co-cultured with FLT3-expressing AML cell lines, in accordance with embodiments of the invention.
Figure 7:
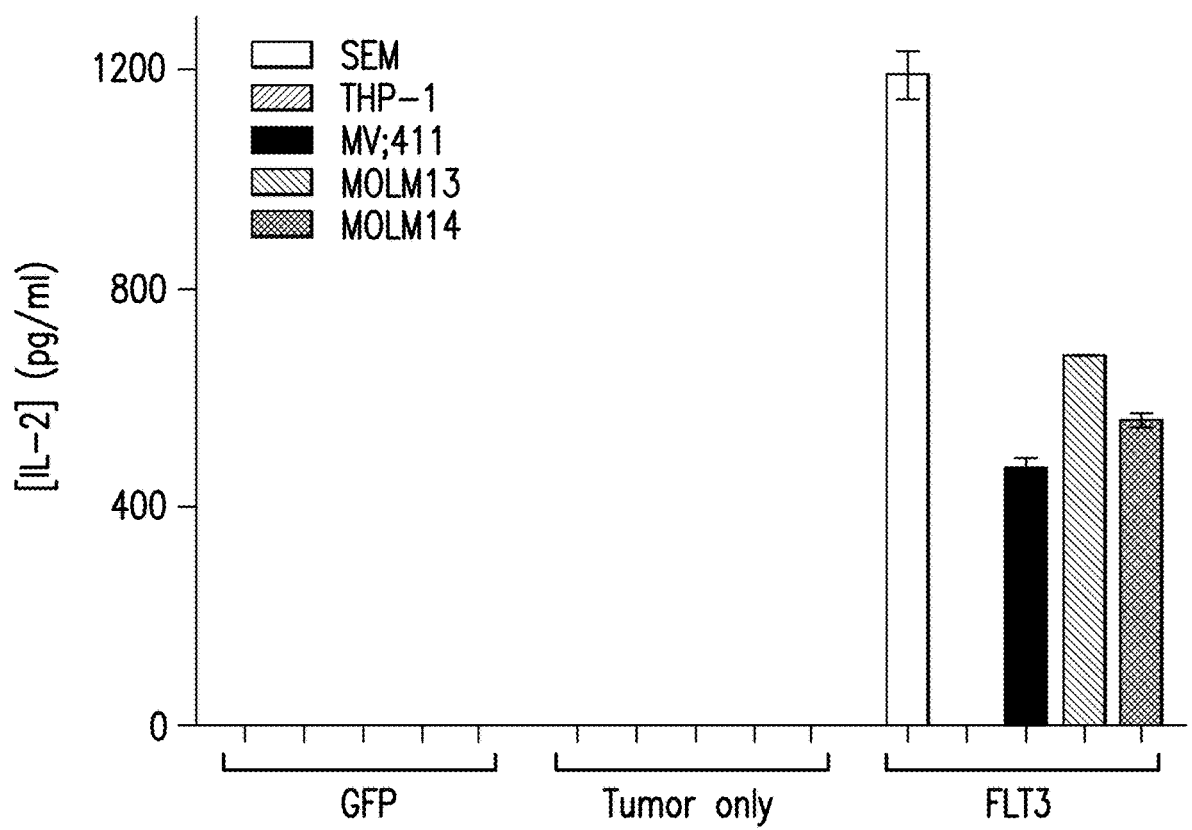
FIG. 7 is a bar graph showing that T cells expressing a FLT3 targeting chimeric antigen receptor secrete high levels of interleukin-2 when co-cultured with FLT3-expressing AML cell lines, in accordance with embodiments of the invention.

The CAR was SEQ ID NO: 1/29. The leader sequence is initially encoded and enhances trafficking to the cell surface; it is likely to be cleaved off in the mature form. The transduction efficiency of GFP and FLT3 CAR transduced T cells were determined on day 9 of T cell culture. GFP transduced T cells were analyzed for GFP positivity by flow cytometry using a LSR Fortessa (BD Biosciences) as shown in the left panel of FIG. 3 (87.8% positive). FLT3 CAR expression was determined using biotinylated protein L (Genscript; Piscataway, NJ, USA) which is a bacterial protein that binds to a subset of kappa light chains of antibodies. The NC7 based FLT3 CAR is a sequence that binds to protein L and the CAR expression can be determined by staining with streptavidin PE (middle panel of FIG. 3, 77.1% positive). As a negative control, FLT3 CAR T cells were stained with secondary streptavidin PE only (right panel of FIG. 3, 0% positive). Data analysis was performed using FlowJo software (FlowJo LLC).

Example 4

This example demonstrates that T cells expressing FLT3-targeting chimeric antigen receptors secrete high levels of cytokines when co-cultured with FLT3-expressing cell lines in accordance with embodiments of the invention.

Cytokine production assay: GFP or CAR transduced T cells were co-cultured with various ALL and AML cell lines with varying expression of FLT3 as determined in Example 1. Acute lymphoblastic and acute myeloid leukemia lines as listed in Example 1 were used as target tumor cell lines to determine the ability of FLT3 CAR T cells to produce Interferon-gamma (IFN-gamma) and Interleukin-2 (IL-2) in response to target recognition and activation of the CAR T cells. The CAR was SEQ ID NO: 1/29. The leader sequence is initially encoded and enhances trafficking to the cell surface; it is likely to be cleaved off in the mature form. T cells (100,000) and leukemia cells (100,000) were co-incubated per well in 96 well plates for 16 hours in 200 mL/well of RPMI 1640 (Invitrogen) media supplemented with 10% heat inactivated fetal bovine serum (Omega Scientific), 100 U/mL penicillin, 100 mg/mL streptomycin, and 2 mM L-glutamine (Invitrogen). The following day the plates were centrifuged at 1200 rpm for 6 minutes, and 150 mL of supernatant was carefully taken for analysis by enzyme linked immunosorbent assay (ELISA). For IFN-gamma the Human IFN-gamma Quantikine ELISA (R&D systems; Minneapolis, MN, USA) was used as per manufacturer's protocol and read on a Spectramax M5 microplate reader (Molecular Devices; Sunnyvale, CA, USA). For IL-2 the Human IL-2 Quantikine ELISA as per manufacturer's protocol (R&D systems; Minneapolis, MN) and read on a Spectramax M5 microplate reader (Molecular Devices). Data was then plotted using GraphPad Prism (GraphPad Software). FIGS. 4-7 show the results.

Example 5

This example demonstrates that T cells expressing FLT3 targeting CARs are able to reduce FLT3 expressing ALL in vivo, an in vivo dose titration of FLT3 CAR T cells, and that T cells expressing FLT3 targeting CARs are able to delay the progression of FLT3 expressing AML in vivo in accordance with embodiments of the invention.

Studies in animals were performed under protocols approved by the NCI Bethesda Animal Care and Use Committee. One million luciferase positive ALL or AML cell lines were intravenously (IV) injected into NSG mice (NOD scid gamma, NOD.Cg-Prkdc$^{scid}$ Il2$^{rgtmIWjl}$/SzJ) (The Jackson Laboratory; Bar Harbor, ME, USA) and monitored for leukemia progression by bioluminescence using a Xenogen IVIS Lumina imaging system (Caliper Life Sciences; Hopkinton, MA, USA). NSG mice with leukemia were imaged for 4 minutes after intraperitoneal (IP) injection with 3 mg D-luciferin (Caliper Life Sciences) for 1 minute. Living Image software (Caliper Life Sciences) was used to analyze the bioluminescent signal from animals with leukemia as photons/s/cm$^2$/sr. GFP or FLT3 CAR transduced T cells were injected on the same day, as described below, when a detectable amount of leukemia was observed and the leukemia progression or regression was measured twice a week. The CAR was SEQ ID NO: 1/29. The leader sequence is initially encoded and enhances trafficking to the cell surface; it is likely to be cleaved off in the mature form.

Figure 8:
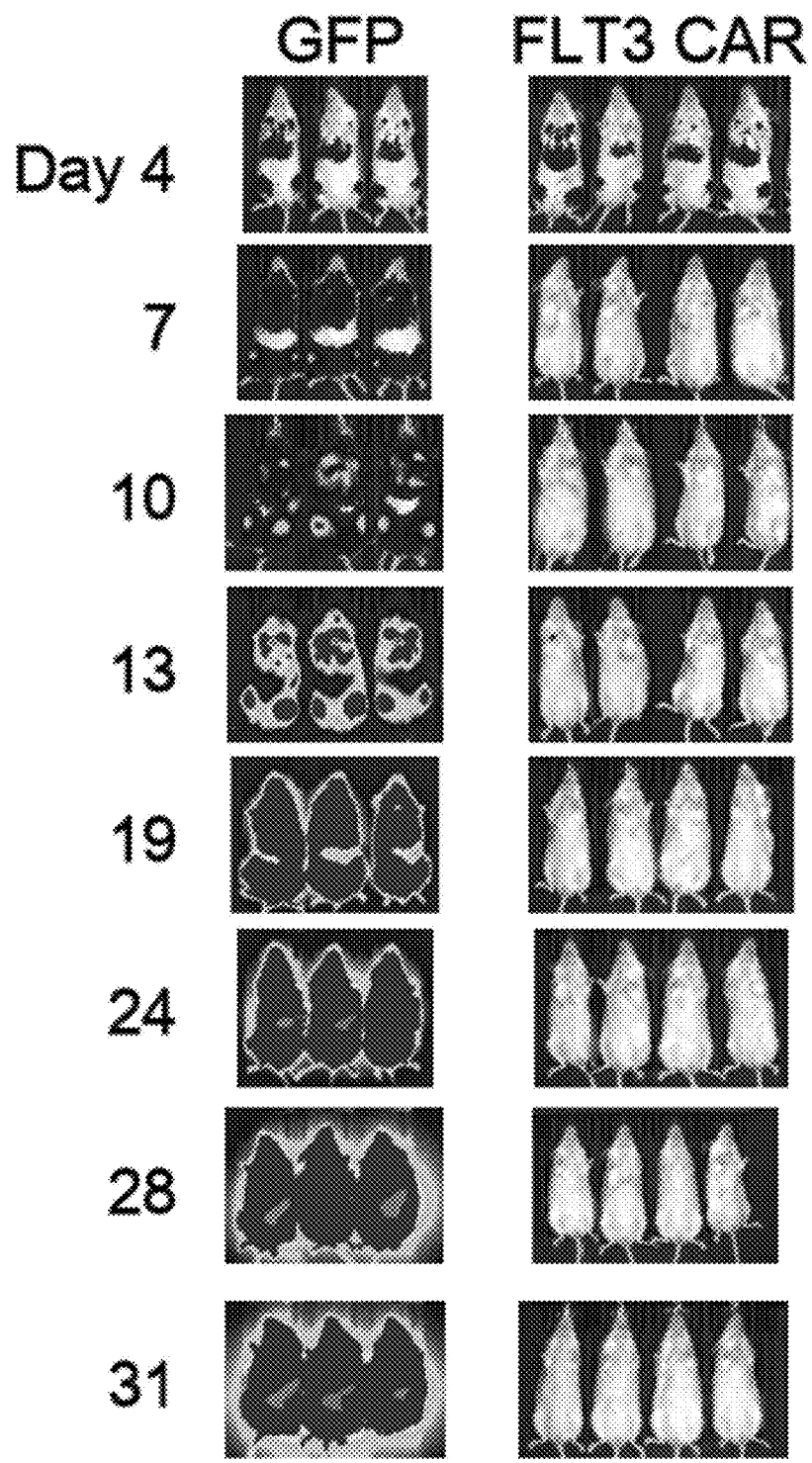
FIG. 8 presents images showing that T cells expressing FLT3 targeting CARs are able to reduce FLT3 expressing ALL in vivo, in accordance with embodiments of the invention.

IV injection of SEM ALL cells: 7.5×10$^6$ GFP-(67% transduction) or FLT3-(50% transduction) CAR transduced T cells were injected on day 4 when a detectable amount of leukemia was observed and the leukemia progression or regression was measured. The results are shown in FIG. 8 (min/max of photons/s/cm$^2$/sr signal: 8.00e4/8.00e6).

Figure 9:
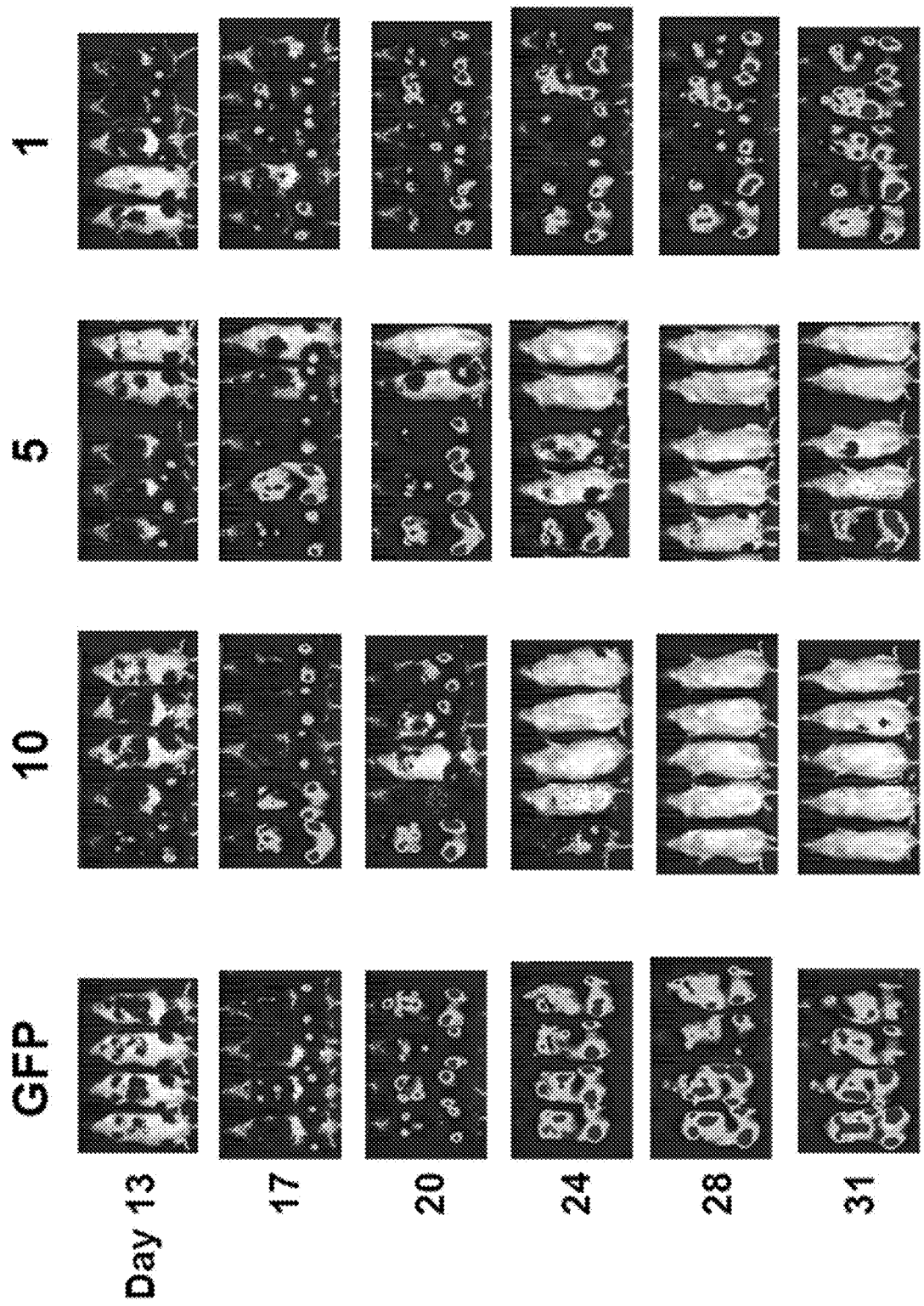
FIG. 9 presents images showing in vivo dose titration of FLT3 CART cells ($10 \times 10^6$ cells (column "10"), $5 \times 10^6$ cells (column "5"), or $1 \times 10^6$ cells (column "1")), in accordance with embodiments of the invention.

IV injection of SEM ALL cells: $10 \times 10^6$ GFP or $10 \times 10^6$, $5 \times 10^6$ or $1 \times 10^6$ FLT3 CAR transduced T cells were injected on day 14 when a detectable amount of leukemia was observed and the leukemia progression or regression was measured. The results are shown in FIG. 9 (min/max of photons/s/cm²/sr signal: 5.00e4/8.00e6).

Figure 10:
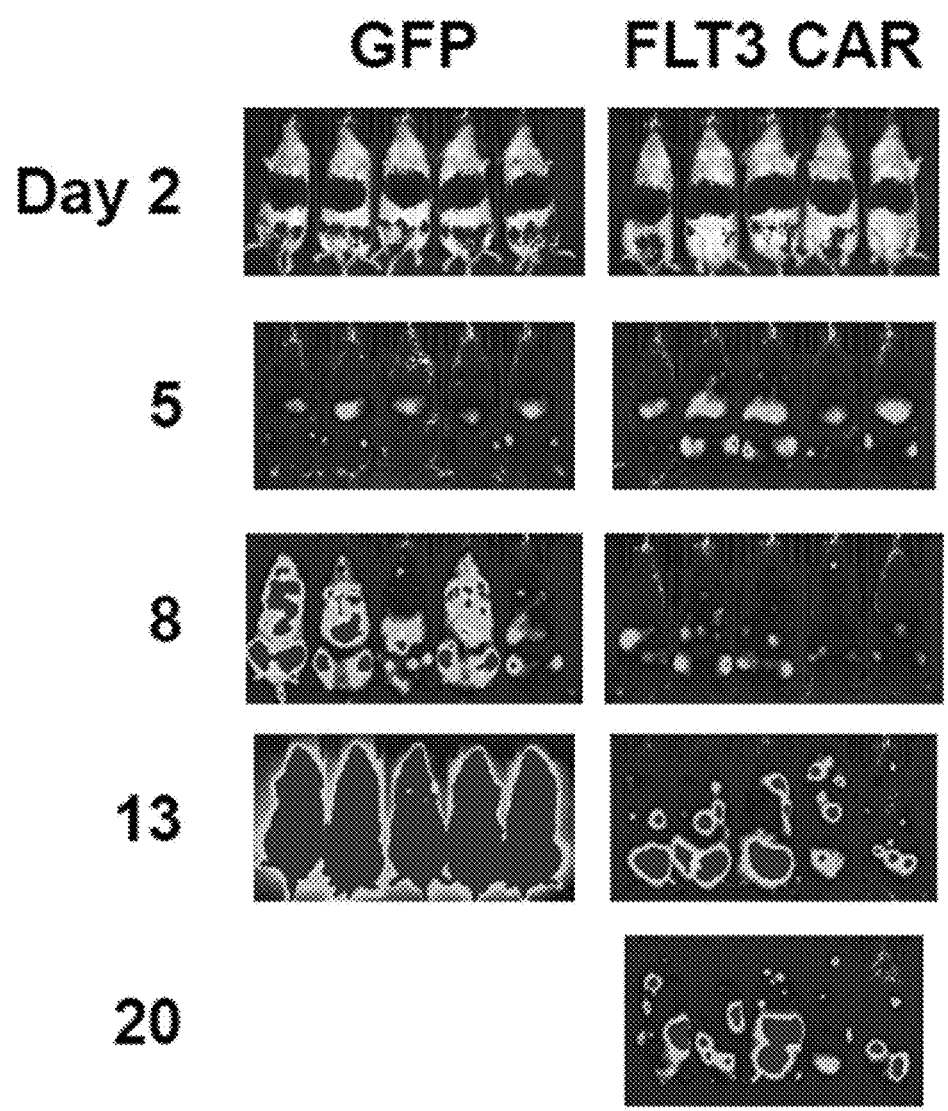
FIG. 10 presents images showing that T cells expressing FLT3 targeting CARs are able to delay the progression of FLT3 expressing AML in vivo, in accordance with embodiments of the invention.

IV injection of MOLM13 AML cells: $7 \times 10^6$ GFP or FLT3 CAR transduced T cells were injected on day 6 when a detectable amount of leukemia was observed and the leukemia progression or regression was measured. The results are shown in FIG. 10 (min/max of photons/s/cm²/sr signal: 5.00e4/8.00e6).

Figure 11:
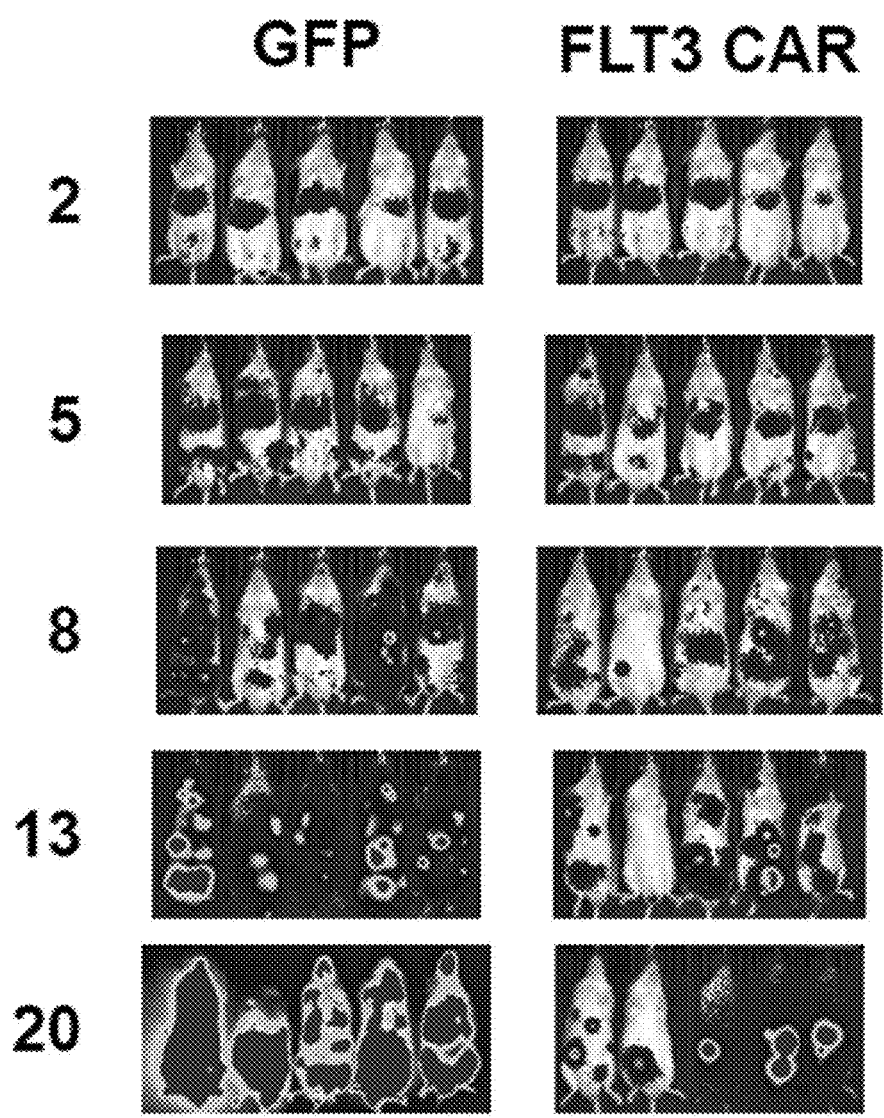
FIG. 11 presents images showing that T cells expressing FLT3 targeting CARs are able to delay the progression of FLT3 expressing AML in vivo, in accordance with embodiments of the invention.

IV injection of MOLM14 AML cells: $7 \times 10^6$ GFP or FLT3 CAR transduced T cells were injected on day 6 when a detectable amount of leukemia was observed and the leukemia progression or regression was measured. The results are shown in FIG. 11 (min/max of photons/s/cm²/sr signal: 5.00e4/8.00e6).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated NK cell comprising a chimeric antigen receptor (CAR),
   wherein the CAR comprises an antigen binding domain specific for FLT3, a transmembrane domain, and an intracellular T cell signaling domain,
   wherein the antigen binding domain comprises a single chain variable fragment (scFv) comprising from N-terminus to C-terminus (a) the heavy chain variable region CDR1, CDR2, and CDR3 sequences of SEQ ID NOS: 6, 8, and 10 and (b) the light chain variable region CDR1, CDR2, and CDR3 sequences of SEQ ID NOS: 14, 16, and 18.

2. The NK cell of claim 1, wherein the antigen binding domain comprises a light chain variable region comprising the sequences of SEQ ID NOS: 13-19.

3. The NK cell of claim 1, wherein the antigen binding domain comprises the heavy chain variable region comprising the sequences of SEQ ID NOS: 5-11.

4. The NK cell of claim 1, wherein the antigen binding domain comprises SEQ ID NOS: 5-19.

5. The NK cell of claim 1, wherein the CAR further comprises a CD8α hinge comprising the sequence of SEQ ID NO: 25.

6. The NK cell of claim 1, wherein the CAR comprises a CD8 transmembrane domain comprising the amino acid sequence of SEQ ID NO: 26.

7. The NK cell of claim 1, wherein the intracellular T cell signaling domain comprises the CD3ζ amino acid sequence of SEQ ID NO: 28.

8. The NK cell of claim 1, wherein the CAR further comprises a CD28 domain.

9. The NK cell of claim 1, wherein the CAR further comprises:
   a CD8α hinge comprising the sequence of SEQ ID NO: 25,
   a CD8 transmembrane domain comprising the amino acid sequence of SEQ ID NO: 26, wherein the intracellular T cell signaling domain comprises the CD3 zeta amino acid sequence of SEQ ID NO: 28, and
   a CD28 domain.

10. The NK cell of claim 9, wherein the cell is allogeneic.

11. A population of NK cells comprising the NK cell of claim 1.

12. A population of NK cells comprising the NK cell of claim 9.

13. A population of NK cells modified to express a chimeric antigen receptor (CAR),
    wherein the CAR comprises an antigen binding domain specific for FLT3, a transmembrane domain, and an intracellular T cell signaling domain,
    wherein the antigen binding domain comprises a single chain variable fragment (scFv) comprising from N-terminus to C-terminus (a) the heavy chain variable region CDR1, CDR2, and CDR3 sequences of SEQ ID NOS: 6, 8, and 10 and (b) the light chain variable region CDR1, CDR2, and CDR3 sequences of SEQ ID NOS: 14, 16, and 18.

14. The population of NK cells of claim 13, wherein the CAR further comprises:
    a CD8α hinge comprising the sequence of SEQ ID NO: 25,
    a CD8 transmembrane domain comprising the amino acid sequence of SEQ ID NO: 26, wherein the intracellular T cell signaling domain comprises the CD3 zeta amino acid sequence of SEQ ID NO: 28, and
    a CD28 domain.

15. A pharmaceutical composition comprising the NK cell of claim 1, and a pharmaceutically acceptable carrier.

16. A pharmaceutical composition comprising the NK cell of claim 9 and a pharmaceutically acceptable carrier.

17. A pharmaceutical composition comprising the population of NK cells of claim 13, and a pharmaceutically acceptable carrier.

18. A pharmaceutical composition comprising the population of NK cells of claim 14, and a pharmaceutically acceptable carrier.

19. A method of treating a subject having acute myeloid leukemia (AML), the method comprising administering to the subject a therapeutically effective amount of the NK cell of claim 9 or a population thereof.

* * * * *